United States Patent
Linsley et al.

(10) Patent No.: US 9,944,926 B2
(45) Date of Patent: Apr. 17, 2018

(54) INDUCED EXON INCLUSION IN SPINAL MUSCLE ATROPHY

(71) Applicant: Sarepta Therapeutics, Inc., Bothell, WA (US)

(72) Inventors: Peter Linsley, Seattle, WA (US); Brian James Leppert, Kenmore, WA (US)

(73) Assignee: Sarepta Therapeutics, Inc., Bothell, WA (US)

( * ) Notice: Subject to any disclaimer, the term of this patent is extended or adjusted under 35 U.S.C. 154(b) by 264 days.

(21) Appl. No.: 14/360,895

(22) PCT Filed: Nov. 30, 2012

(86) PCT No.: PCT/US2012/067475
§ 371 (c)(1),
(2) Date: May 27, 2014

(87) PCT Pub. No.: WO2013/082551
PCT Pub. Date: Jun. 6, 2013

(65) Prior Publication Data
US 2014/0329772 A1    Nov. 6, 2014

Related U.S. Application Data

(60) Provisional application No. 61/565,499, filed on Nov. 30, 2011.

(51) Int. Cl.
*C12N 15/113* (2010.01)
*C12N 15/11* (2006.01)

(52) U.S. Cl.
CPC .......... *C12N 15/113* (2013.01); *C12N 15/111* (2013.01); *C12N 2310/11* (2013.01); *C12N 2310/31* (2013.01); *C12N 2310/314* (2013.01); *C12N 2310/3233* (2013.01); *C12N 2320/33* (2013.01)

(58) Field of Classification Search
None
See application file for complete search history.

(56) References Cited

U.S. PATENT DOCUMENTS

| 9,161,948 | B2 | 10/2015 | Hanson |
| 2004/0006089 | A1 | 1/2004 | Thurieau et al. |
| 2006/0287268 | A1 | 12/2006 | Iversen et al. |
| 2008/0194463 | A1 | 8/2008 | Weller et al. |
| 2010/0016215 | A1* | 1/2010 | Moulton ............... C12N 15/87 514/1.1 |
| 2011/0269820 | A1 | 11/2011 | Singh et al. |
| 2014/0303238 | A1 | 10/2014 | Linsley et al. |

FOREIGN PATENT DOCUMENTS

| JP | 2003-516965 A | 5/2003 |
| JP | 2011-236157 A | 11/2011 |
| WO | 2007/002390 A2 | 1/2007 |
| WO | 2008/018795 A1 | 2/2008 |
| WO | 2008/036127 A2 | 3/2008 |
| WO | 2010/120820 A1 | 10/2010 |
| WO | 2011/150408 A2 | 12/2011 |
| WO | 2012/150960 A1 | 11/2012 |
| WO | 2013/1082551 A1 | 6/2013 |

OTHER PUBLICATIONS

European Office Action, EP Application No. 12812432.8-1401, dated Apr. 1, 2016, 5 pages.
International Preliminary Report on Patentability, PCT/US2012/067470, dated Jun. 30, 2014, pp. 1-7.
International Search Report and Written Opinion, PCT/US2012/067470, dated Mar. 28, 2013, pp. 1-11.
Prabahar, K. et al., "Effect of Phosphate Activating Group on Oligonucleotide Formation on Montmorillonite: The Regioselective Formation of 3' 5'-Linked Oligoadenylates," J. Am. Chem. Soc., vol. 116: 10914-10920 (1994).
Singh, N. et al., "A short antisense oligonucleotide masking a unique intronic motif prevents skipping of a critical exon in spinal muscular atrophy," RNA Biology, vol. 6(3): 341-350 (2009).
Burghes, A.H.M., et al., "Antisense oligonucleotides and spinal muscular atrophy: skipping along", Genes & Development, vol. 24, No. 15, Aug. 1, 2010, pp. 1574-1579, XP55044388, ISSN: 0890-9369, DOI: 10.1101/gad.1961710
Cartegni L. et al., "Correction of disease-associated exon skipping by synthetic exon-specific activators", Nature Structural Biology, Nature Publishing Group, vol. 10, No. 2, Feb. 1, 2003, pp. 120-125, XP002262731, ISSN: 1072-8368, DOI:10.1038/NSB887.
Hua, Yimin, et al., "Enhancement of SMN2 exon 7 inclusion by antisense oligonucleotides targeting the exon", PLOS Biology, Public Library of Science, vol. 5, No. 4, Apr. 1, 2007, p. E73, XP002596113, ISSN: 1544-9173.
International Preliminary Report on Patentability, PCT/2012/067475, dated Jun. 30, 2014, pp. 1-7.
International Search Report, PCT/US2012/067475, dated Mar. 26, 2013, pp. 1-6.
Lim, S.R., et al., "Modulation of Survival Motor Neuron Pre-MRNA Splicing by Inhibition of Alternative 3'Splice Site Pairing," Journal of Biological Chemistry, American Society for Biochemistry and Molecular Biology, vol. 276, No. 48, Nov. 30, 2001, pp. 45476-45483, XP008124558, ISSN: 0021-9258. DOI: 10.1074/JBC.M107632200 [retrieved on Oct. 2, 2001].
Sazani, P. et al., "Nuclear antisense effects of neutral, anionic and cationic oligonucleotide analogs," Nucleic Acids Research, Oxford University Press, vol. 29, No. 19, Oct. 1, 2001, pp. 3965-3974, XP002978135, ISSN: 0305-1048.

(Continued)

*Primary Examiner* — Kimberly Chong
(74) *Attorney, Agent, or Firm* — Finnegan, Henderson, Farabow, Garrett & Dunner, LLP

(57) ABSTRACT

The invention relates to the use of an antisense compound for inducing exon inclusion as a treatment for Spinal Muscle Atrophy (SMA). More particularly it relates to inducing inclusion of exon 7 to restore levels of Survival Motor Neuron (SMN) protein encoded by the Survival Motor Neuron (SMN) gene.

18 Claims, 9 Drawing Sheets

(56) References Cited

OTHER PUBLICATIONS

Singh, N.N. et al., "An antisense microwalk reveals critical role of an intronic position linked to a unique long-distance interaction in pre-mRNA splicing", RNA, vol. 16, No. 6, Jun. 1, 2010, pp. 1167-1181, XP55056239, ISSN: 1355-8382, DOI: 10.1261/rna.2154310.
Swenson, D.L., et al., "Chemical Modifications of Antisense Morpholino Oligomers Enhance Their Efficacy against Ebola Virus Infection," Antimictobial Agents and Chemotherapy, vol. 53, No. 5, May 1, 2009, pp. 2089-2099, XP55056348, ISSN: 0066-4804, DOI: 10.1128/AAC.00936-08.
Japanese Office Action, JP Application No. 2014-544962, dated Sep. 6, 2017. 8 pages.
Kaya, I. et al., "The synthesis and characterization of oligo-N-4-aminopryridine, oligo-2-[(pyridine-4-yl-imino)methyl] phenol and its some oligomer-metal complexes," Polymer, vol. 44:7299-7309 (2003).
U.S. Appl. No. 14/360,890, dated Mar. 9, 2017.

\* cited by examiner

Sequences Tested

| Sequence Name | Sequence (orientation 5' to 3') | Sequence Identifiers |
|---|---|---|
| N1 | A TTC ACT TTC ATA ATG CTG G | SEQ ID NO:1 |
| 14mer | T TTC ATA ATG CTG G | SEQ ID NO:19 |
| 14mer-APN | T TTC ATA ATG CTG G | SEQ ID NO:21 |
|  |  |  |
| E8/4a | C TAG TAT TTC CTG CAA ATG AG | SEQ ID NO:42 |
| E8/4a-APN | C TAG TAT TTC CTG CAA ATG AG | SEQ ID NO:43 |
| E8/4b | C CAG CAT TTC CTG CAA ATG AG | SEQ ID NO:53 |
| E8/4b-APN | C CAG CAT TTC CTG CAA ATG AG | SEQ ID NO:54 |

Figure 5

SEQUENCE LISTING

<160> NUMBER OF SEQ ID NOS: 81

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide: N1

<400> SEQUENCE: 1
attcactttc ataatgctgg                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide: N1-B

```
<400> SEQUENCE: 2
attcactttc ataatgctgg                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide: N1-C

<400> SEQUENCE: 3
attcactttc ataatgctgg                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide: N1-D

<400> SEQUENCE: 4
attcactttc ataatgctgg                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide: N1-E

<400> SEQUENCE: 5
attcactttc ataatgctgg                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide: N1-F

<400> SEQUENCE: 6
attcactttc ataatgctgg                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide: N1-G

<400> SEQUENCE: 7
attcactttc ataatgctgg                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide: N1-H

<400> SEQUENCE: 8
attcactttc ataatgctgg                                               20

<210> SEQ ID NO 9
<211> LENGTH: 17
```

```
<212> TYPE: DNA
<213> ORGANISM: Artificial Sequence
<220> FEATURE:
<223> OTHER INFORMATION: Synthetic oligonucleotide: AVI-17mer

<400> SEQUENCE: 9
cactttcata atgctgg                                                      17

<210> SEQ ID NO 10
<211> LENGTH: 17
<212> TYPE: DNA
<213> ORGANISM: Artificial Sequence
<220> FEATURE:
<223> OTHER INFORMATION: Synthetic oligonucleotide: AVI-17mer-B

<400> SEQUENCE: 10
cactttcata atgctgg                                                      17

<210> SEQ ID NO 11
<211> LENGTH: 17
<212> TYPE: DNA
<213> ORGANISM: Artificial Sequence
<220> FEATURE:
<223> OTHER INFORMATION: Synthetic oligonucleotide: AVI-17mer-C

<400> SEQUENCE: 11
cactttcata atgctgg                                                      17

<210> SEQ ID NO 12
<211> LENGTH: 17
<212> TYPE: DNA
<213> ORGANISM: Artificial Sequence
<220> FEATURE:
<223> OTHER INFORMATION: Synthetic oligonucleotide: AVI-17mer-D

<400> SEQUENCE: 12
cactttcata atgctgg                                                      17

<210> SEQ ID NO 13
<211> LENGTH: 17
<212> TYPE: DNA
<213> ORGANISM: Artificial Sequence
<220> FEATURE:
<223> OTHER INFORMATION: Synthetic oligonucleotide: AVI-17mer-E

<400> SEQUENCE: 13
cactttcata atgctgg                                                      17

<210> SEQ ID NO 14
<211> LENGTH: 17
<212> TYPE: DNA
<213> ORGANISM: Artificial Sequence
<220> FEATURE:
<223> OTHER INFORMATION: Synthetic oligonucleotide: AVI-17mer-F

<400> SEQUENCE: 14
cactttcata atgctgg                                                      17

<210> SEQ ID NO 15
<211> LENGTH: 17
<212> TYPE: DNA
<213> ORGANISM: Artificial Sequence
<220> FEATURE:
<223> OTHER INFORMATION: Synthetic oligonucleotide: AVI-17mer-G

<400> SEQUENCE: 15
```
cactttcata atgctgg                                               17

<210> SEQ ID NO 16
<211> LENGTH: 17
<212> TYPE: DNA
<213> ORGANISM: Artificial Sequence
<220> FEATURE:
<223> OTHER INFORMATION: Synthetic oligonucleotide: AVI-17mer-H

<400> SEQUENCE: 16
cactttcata atgctgg                                               17

<210> SEQ ID NO 17
<211> LENGTH: 17
<212> TYPE: DNA
<213> ORGANISM: Artificial Sequence
<220> FEATURE:
<223> OTHER INFORMATION: Synthetic oligonucleotide: AVI-17mer-I

<400> SEQUENCE: 17
cactttcata atgctgg                                               17

<210> SEQ ID NO 18
<211> LENGTH: 17
<212> TYPE: DNA
<213> ORGANISM: Artificial Sequence
<220> FEATURE:
<223> OTHER INFORMATION: Synthetic oligonucleotide: AVI-17mer-J

<400> SEQUENCE: 18
cactttcata atgctgg                                               17

<210> SEQ ID NO 19
<211> LENGTH: 14
<212> TYPE: DNA
<213> ORGANISM: Artificial Sequence
<220> FEATURE:
<223> OTHER INFORMATION: Synthetic oligonucleotide: 14mer

<400> SEQUENCE: 19
tttcataatg ctgg                                                  14

<210> SEQ ID NO 20
<211> LENGTH: 14
<212> TYPE: DNA
<213> ORGANISM: Artificial Sequence
<220> FEATURE:
<223> OTHER INFORMATION: Synthetic oligonucleotide: 14mer-B

<400> SEQUENCE: 20
tttcataatg ctgg                                                  14

<210> SEQ ID NO 21
<211> LENGTH: 14
<212> TYPE: DNA
<213> ORGANISM: Artificial Sequence
<220> FEATURE:
<223> OTHER INFORMATION: Synthetic oligonucleotide: 14mer-APN

<400> SEQUENCE: 21
tttcataatg ctgg                                                  14

<210> SEQ ID NO 22
<211> LENGTH: 14
<212> TYPE: DNA
<213> ORGANISM: Artificial Sequence

```
<220> FEATURE:
<223> OTHER INFORMATION: Synthetic oligonucleotide: 14mer-C

<400> SEQUENCE: 22
tttcataatg ctgg                                              14

<210> SEQ ID NO 23
<211> LENGTH: 14
<212> TYPE: DNA
<213> ORGANISM: Artificial Sequence
<220> FEATURE:
<223> OTHER INFORMATION: Synthetic oligonucleotide: 14mer-D

<400> SEQUENCE: 23
tttcataatg ctgg                                              14

<210> SEQ ID NO 24
<211> LENGTH: 14
<212> TYPE: DNA
<213> ORGANISM: Artificial Sequence
<220> FEATURE:
<223> OTHER INFORMATION: Synthetic oligonucleotide: 14mer-E

<400> SEQUENCE: 24
tttcataatg ctgg                                              14

<210> SEQ ID NO 25
<211> LENGTH: 14
<212> TYPE: DNA
<213> ORGANISM: Artificial Sequence
<220> FEATURE:
<223> OTHER INFORMATION: Synthetic oligonucleotide: 14mer-F

<400> SEQUENCE: 25
tttcataatg ctgg                                              14

<210> SEQ ID NO 26
<211> LENGTH: 11
<212> TYPE: DNA
<213> ORGANISM: Artificial Sequence
<220> FEATURE:
<223> OTHER INFORMATION: Synthetic oligonucleotide: 3UP11

<400> SEQUENCE: 26
aatgctggca g                                                 11

<210> SEQ ID NO 27
<211> LENGTH: 11
<212> TYPE: DNA
<213> ORGANISM: Artificial Sequence
<220> FEATURE:
<223> OTHER INFORMATION: Synthetic oligonucleotide: 11mer-APN

<400> SEQUENCE: 27
aatgctggca g                                                 11

<210> SEQ ID NO 28
<211> LENGTH: 11
<212> TYPE: DNA
<213> ORGANISM: Artificial Sequence
<220> FEATURE:
<223> OTHER INFORMATION: Synthetic oligonucleotide: 11mer-B

<400> SEQUENCE: 28
aatgctggca g                                                 11
```

```
<210> SEQ ID NO 29
<211> LENGTH: 11
<212> TYPE: DNA
<213> ORGANISM: Artificial Sequence
<220> FEATURE:
<223> OTHER INFORMATION: Synthetic oligonucleotide: 11mer-C

<400> SEQUENCE: 29
aatgctggca g                                                              11

<210> SEQ ID NO 30
<211> LENGTH: 11
<212> TYPE: DNA
<213> ORGANISM: Artificial Sequence
<220> FEATURE:
<223> OTHER INFORMATION: Synthetic oligonucleotide: 11mer-D

<400> SEQUENCE: 30
aatgctggca g                                                              11

<210> SEQ ID NO 31
<211> LENGTH: 11
<212> TYPE: DNA
<213> ORGANISM: Artificial Sequence
<220> FEATURE:
<223> OTHER INFORMATION: Synthetic oligonucleotide: 11mer-E

<400> SEQUENCE: 31
aatgctggca g                                                              11

<210> SEQ ID NO 32
<211> LENGTH: 11
<212> TYPE: DNA
<213> ORGANISM: Artificial Sequence
<220> FEATURE:
<223> OTHER INFORMATION: Synthetic oligonucleotide: 11mer-F

<400> SEQUENCE: 32
aatgctggca g                                                              11

<210> SEQ ID NO 33
<211> LENGTH: 8
<212> TYPE: DNA
<213> ORGANISM: Artificial Sequence
<220> FEATURE:
<223> OTHER INFORMATION: Synthetic oligonucleotide: 3UP8

<400> SEQUENCE: 33 gctggcag                                                                   8

<210> SEQ ID NO 34
<211> LENGTH: 8
<212> TYPE: DNA
<213> ORGANISM: Artificial Sequence
<220> FEATURE:
<223> OTHER INFORMATION: Synthetic oligonucleotide: 8mer-APN

<400> SEQUENCE: 34 gctggcag                                                                   8

<210> SEQ ID NO 35
<211> LENGTH: 8
<212> TYPE: DNA
<213> ORGANISM: Artificial Sequence
<220> FEATURE:
<223> OTHER INFORMATION: Synthetic oligonucleotide: 8mer-B
```

-continued

```
<400> SEQUENCE: 35 gctggcag                                                              8

<210> SEQ ID NO 36
<211> LENGTH: 8
<212> TYPE: DNA
<213> ORGANISM: Artificial Sequence
<220> FEATURE:
<223> OTHER INFORMATION: Synthetic oligonucleotide: 8mer-C

<400> SEQUENCE: 36 gctggcag                                                              8

<210> SEQ ID NO 37
<211> LENGTH: 8
<212> TYPE: DNA
<213> ORGANISM: Artificial Sequence
<220> FEATURE:
<223> OTHER INFORMATION: Synthetic oligonucleotide: 8mer-D

<400> SEQUENCE: 37 gctggcag                                                              8

<210> SEQ ID NO 38
<211> LENGTH: 8
<212> TYPE: DNA
<213> ORGANISM: Artificial Sequence
<220> FEATURE:
<223> OTHER INFORMATION: Synthetic oligonucleotide: 8mer-E

<400> SEQUENCE: 38 gctggcag                                                              8

<210> SEQ ID NO 39
<211> LENGTH: 8
<212> TYPE: DNA
<213> ORGANISM: Artificial Sequence
<220> FEATURE:
<223> OTHER INFORMATION: Synthetic oligonucleotide: 8mer-F

<400> SEQUENCE: 39 gctggcag                                                              8

<210> SEQ ID NO 40
<211> LENGTH: 8
<212> TYPE: DNA
<213> ORGANISM: Artificial Sequence
<220> FEATURE:
<223> OTHER INFORMATION: Synthetic oligonucleotide: 8mer-G

<400> SEQUENCE: 40 gctggcag                                                              8

<210> SEQ ID NO 41
<211> LENGTH: 8
<212> TYPE: DNA
<213> ORGANISM: Artificial Sequence
<220> FEATURE:
<223> OTHER INFORMATION: Synthetic oligonucleotide: 8mer-H

<400> SEQUENCE: 41 gctggcag                                                              8

<210> SEQ ID NO 42
```

<210> SEQ ID NO 42
<211> LENGTH: 21
<212> TYPE: DNA
<213> ORGANISM: Artificial Sequence
<220> FEATURE:
<223> OTHER INFORMATION: Synthetic oligonucleotide: E8/4a

<400> SEQUENCE: 42
ctagtatttc ctgcaaatga g                                    21

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide: E8/4a-APN

<400> SEQUENCE: 43
ctagtatttc ctgcaaatga g                                    21

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide: E8/4a-B

<400> SEQUENCE: 44
ctagtatttc ctgcaaatga g                                    21

<210> SEQ ID NO 45
<211> LENGTH: 21
<212> TYPE: DNA
<213> ORGANISM: Artificial Sequence
<220> FEATURE:
<223> OTHER INFORMATION: Synthetic oligonucleotide: E8/4a-C

<400> SEQUENCE: 45
ctagtatttc ctgcaaatga g                                    21

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide: E8/4a-D

<400> SEQUENCE: 46
ctagtatttc ctgcaaatga g                                    21

<210> SEQ ID NO 47
<211> LENGTH: 21
<212> TYPE: DNA
<213> ORGANISM: Artificial Sequence
<220> FEATURE:
<223> OTHER INFORMATION: Synthetic oligonucleotide: E8/4a-E

<400> SEQUENCE: 47
ctagtatttc ctgcaaatga g                                    21

<210> SEQ ID NO 48
<211> LENGTH: 21
<212> TYPE: DNA
<213> ORGANISM: Artificial Sequence
<220> FEATURE:
<223> OTHER INFORMATION: Synthetic oligonucleotide: E8/4a-F

<400> SEQUENCE: 48

```
ctagtatttc ctgcaaatga g                                              21

<210> SEQ ID NO 49
<211> LENGTH: 21
<212> TYPE: DNA
<213> ORGANISM: Artificial Sequence
<220> FEATURE:
<223> OTHER INFORMATION: Synthetic oligonucleotide: E8/4a-G

<400> SEQUENCE: 49
ctagtatttc ctgcaaatga g                                              21

<210> SEQ ID NO 50
<211> LENGTH: 21
<212> TYPE: DNA
<213> ORGANISM: Artificial Sequence
<220> FEATURE:
<223> OTHER INFORMATION: Synthetic oligonucleotide: E8/4a-H

<400> SEQUENCE: 50
ctagtatttc ctgcaaatga g                                              21

<210> SEQ ID NO 51
<211> LENGTH: 21
<212> TYPE: DNA
<213> ORGANISM: Artificial Sequence
<220> FEATURE:
<223> OTHER INFORMATION: Synthetic oligonucleotide: E8/4a-I

<400> SEQUENCE: 51
ctagtatttc ctgcaaatga g                                              21

<210> SEQ ID NO 52
<211> LENGTH: 21
<212> TYPE: DNA
<213> ORGANISM: Artificial Sequence
<220> FEATURE:
<223> OTHER INFORMATION: Synthetic oligonucleotide: E8/4a-J

<400> SEQUENCE: 52
ctagtatttc ctgcaaatga g                                              21

<210> SEQ ID NO 53
<211> LENGTH: 21
<212> TYPE: DNA
<213> ORGANISM: Artificial Sequence
<220> FEATURE:
<223> OTHER INFORMATION: Synthetic oligonucleotide: E8/4b

<400> SEQUENCE: 53
ccagcatttc ctgcaaatga g                                              21

<210> SEQ ID NO 54
<211> LENGTH: 21
<212> TYPE: DNA
<213> ORGANISM: Artificial Sequence
<220> FEATURE:
<223> OTHER INFORMATION: Synthetic oligonucleotide: E8/4b-APN

<400> SEQUENCE: 54
ccagcatttc ctgcaaatga g                                              21

<210> SEQ ID NO 55
<211> LENGTH: 21
<212> TYPE: DNA
```

<210> SEQ ID NO 55
<211> LENGTH: 21
<212> TYPE: DNA
<213> ORGANISM: Artificial Sequence
<220> FEATURE:
<223> OTHER INFORMATION: Synthetic oligonucleotide: E8/4b-B

<400> SEQUENCE: 55
ccagcatttc ctgcaaatga g                                    21

<210> SEQ ID NO 56
<211> LENGTH: 21
<212> TYPE: DNA
<213> ORGANISM: Artificial Sequence
<220> FEATURE:
<223> OTHER INFORMATION: Synthetic oligonucleotide: E8/4b-C

<400> SEQUENCE: 56
ccagcatttc ctgcaaatga g                                    21

<210> SEQ ID NO 57
<211> LENGTH: 21
<212> TYPE: DNA
<213> ORGANISM: Artificial Sequence
<220> FEATURE:
<223> OTHER INFORMATION: Synthetic oligonucleotide: E8/4b-D

<400> SEQUENCE: 57
ccagcatttc ctgcaaatga g                                    21

<210> SEQ ID NO 58
<211> LENGTH: 21
<212> TYPE: DNA
<213> ORGANISM: Artificial Sequence
<220> FEATURE:
<223> OTHER INFORMATION: Synthetic oligonucleotide: E8/4b-E

<400> SEQUENCE: 58
ccagcatttc ctgcaaatga g                                    21

<210> SEQ ID NO 59
<211> LENGTH: 21
<212> TYPE: DNA
<213> ORGANISM: Artificial Sequence
<220> FEATURE:
<223> OTHER INFORMATION: Synthetic oligonucleotide: E8/4b-F

<400> SEQUENCE: 59
ccagcatttc ctgcaaatga g                                    21

<210> SEQ ID NO 60
<211> LENGTH: 21
<212> TYPE: DNA
<213> ORGANISM: Artificial Sequence
<220> FEATURE:
<223> OTHER INFORMATION: Synthetic oligonucleotide: E8/4b-G

<400> SEQUENCE: 60
ccagcatttc ctgcaaatga g                                    21

<210> SEQ ID NO 61
<211> LENGTH: 21
<212> TYPE: DNA
<213> ORGANISM: Artificial Sequence
<220> FEATURE:
<223> OTHER INFORMATION: Synthetic oligonucleotide: E8/4b-H

<400> SEQUENCE: 61
ccagcatttc ctgcaaatga g                                    21

<210> SEQ ID NO 62
<211> LENGTH: 25
<212> TYPE: DNA
<213> ORGANISM: Artificial Sequence
<220> FEATURE:
<223> OTHER INFORMATION: Synthetic oligonucleotide: E8/3

<400> SEQUENCE: 62
atgccagcat ttcctgcaaa tgaga                                                25

<210> SEQ ID NO 63
<211> LENGTH: 25
<212> TYPE: DNA
<213> ORGANISM: Artificial Sequence
<220> FEATURE:
<223> OTHER INFORMATION: Synthetic oligonucleotide: E8/3-B

<400> SEQUENCE: 63
atgccagcat ttcctgcaaa tgaga                                                25

<210> SEQ ID NO 64
<211> LENGTH: 25
<212> TYPE: DNA
<213> ORGANISM: Artificial Sequence
<220> FEATURE:
<223> OTHER INFORMATION: Synthetic oligonucleotide: E8/3-C

<400> SEQUENCE: 64
atgccagcat ttcctgcaaa tgaga                                                25

<210> SEQ ID NO 65
<211> LENGTH: 25
<212> TYPE: DNA
<213> ORGANISM: Artificial Sequence
<220> FEATURE:
<223> OTHER INFORMATION: Synthetic oligonucleotide: E8/3-D

<400> SEQUENCE: 65
atgccagcat ttcctgcaaa tgaga                                                25

<210> SEQ ID NO 66
<211> LENGTH: 25
<212> TYPE: DNA
<213> ORGANISM: Artificial Sequence
<220> FEATURE:
<223> OTHER INFORMATION: Synthetic oligonucleotide: E8/3-E

<400> SEQUENCE: 66
atgccagcat ttcctgcaaa tgaga                                                25

<210> SEQ ID NO 67
<211> LENGTH: 25
<212> TYPE: DNA
<213> ORGANISM: Artificial Sequence
<220> FEATURE:
<223> OTHER INFORMATION: Synthetic oligonucleotide: E8/3-F

<400> SEQUENCE: 67
atgccagcat ttcctgcaaa tgaga                                                25

<210> SEQ ID NO 68
<211> LENGTH: 25
<212> TYPE: DNA
<213> ORGANISM: Artificial Sequence
<220> FEATURE:

<223> OTHER INFORMATION: Synthetic oligonucleotide: E8/3-G

<400> SEQUENCE: 68
atgccagcat ttcctgcaaa tgaga                                              25

<210> SEQ ID NO 69
<211> LENGTH: 25
<212> TYPE: DNA
<213> ORGANISM: Artificial Sequence
<220> FEATURE:
<223> OTHER INFORMATION: Synthetic oligonucleotide: E8/3-H

<400> SEQUENCE: 69
atgccagcat ttcctgcaaa tgaga                                              25

<210> SEQ ID NO 70
<211> LENGTH: 25
<212> TYPE: DNA
<213> ORGANISM: Artificial Sequence
<220> FEATURE:
<223> OTHER INFORMATION: Synthetic oligonucleotide: E8/4

<400> SEQUENCE: 70
gctctatgcc agcatttcct gcaaa                                              25

<210> SEQ ID NO 71
<211> LENGTH: 25
<212> TYPE: DNA
<213> ORGANISM: Artificial Sequence
<220> FEATURE:
<223> OTHER INFORMATION: Synthetic oligonucleotide: E8/4-B

<400> SEQUENCE: 71
gctctatgcc agcatttcct gcaaa                                              25

<210> SEQ ID NO 72
<211> LENGTH: 25
<212> TYPE: DNA
<213> ORGANISM: Artificial Sequence
<220> FEATURE:
<223> OTHER INFORMATION: Synthetic oligonucleotide: E8/4-C

<400> SEQUENCE: 72
gctctatgcc agcatttcct gcaaa                                              25

<210> SEQ ID NO 73
<211> LENGTH: 25
<212> TYPE: DNA
<213> ORGANISM: Artificial Sequence
<220> FEATURE:
<223> OTHER INFORMATION: Synthetic oligonucleotide: E8/4-D

<400> SEQUENCE: 73
gctctatgcc agcatttcct gcaaa                                              25

<210> SEQ ID NO 74
<211> LENGTH: 25
<212> TYPE: DNA
<213> ORGANISM: Artificial Sequence
<220> FEATURE:
<223> OTHER INFORMATION: Synthetic oligonucleotide: E8/4-E

<400> SEQUENCE: 74
gctctatgcc agcatttcct gcaaa                                              25

```
<210> SEQ ID NO 75
<211> LENGTH: 25
<212> TYPE: DNA
<213> ORGANISM: Artificial Sequence
<220> FEATURE:
<223> OTHER INFORMATION: Synthetic oligonucleotide: E8/4-F

<400> SEQUENCE: 75
gctctatgcc agcatttcct gcaaa                                              25

<210> SEQ ID NO 76
<211> LENGTH: 25
<212> TYPE: DNA
<213> ORGANISM: Artificial Sequence
<220> FEATURE:
<223> OTHER INFORMATION: Synthetic oligonucleotide: E8/4-G

<400> SEQUENCE: 76
gctctatgcc agcatttcct gcaaa                                              25

<210> SEQ ID NO 77
<211> LENGTH: 25
<212> TYPE: DNA
<213> ORGANISM: Artificial Sequence
<220> FEATURE:
<223> OTHER INFORMATION: Synthetic oligonucleotide: E8/4-H

<400> SEQUENCE: 77
gctctatgcc agcatttcct gcaaa                                              25

<210> SEQ ID NO 78
<211> LENGTH: 25
<212> TYPE: DNA
<213> ORGANISM: Artificial Sequence
<220> FEATURE:
<223> OTHER INFORMATION: Synthetic oligonucleotide: E8/4-I

<400> SEQUENCE: 78
gctctatgcc agcatttcct gcaaa                                              25

<210> SEQ ID NO 79
<211> LENGTH: 25
<212> TYPE: DNA
<213> ORGANISM: Artificial Sequence
<220> FEATURE:
<223> OTHER INFORMATION: Synthetic oligonucleotide: E8/4-J

<400> SEQUENCE: 79
gctctatgcc agcatttcct gcaaa                                              25

<210> SEQ ID NO 80
<211> LENGTH: 21
<212> TYPE: DNA
<213> ORGANISM: Artificial Sequence
<220> FEATURE:
<223> OTHER INFORMATION: Synthetic oligonucleotide: E6-F

<400> SEQUENCE: 80
ataattcccc caccacctcc c                                                  21

<210> SEQ ID NO 81
<211> LENGTH: 22
<212> TYPE: DNA
```

```
<213> ORGANISM: Artificial Sequence
<220> FEATURE:
<223> OTHER INFORMATION: Synthetic oligonucleotide: E8-467-R

<400> SEQUENCE: 81
ttgccacata cgcctcacat ac                                          22
```

INDUCED EXON INCLUSION IN SPINAL MUSCLE ATROPHY

RELATED APPLICATIONS

This application is a 35 U.S.C. 371 national stage filing of International Application PCT/US2012/067475, filed Nov. 30, 2012, which claims priority to U.S. Provisional Patent Application 61/565,499 filed Nov. 30, 2011. The contents of the aforementioned applications are hereby incorporated by reference herein in their entirety.

FIELD OF THE INVENTION

The invention relates to the use of an antisense compound for inducing exon inclusion as a treatment for Spinal Muscle Atrophy (SMA). More particularly it relates to inducing inclusion of exon 7 to restore levels of Survival Motor Neuron (SMN) protein encoded by the Survival Motor Neuron (SMN) gene.

BACKGROUND

Alternative splicing increases the coding potential of human genome by producing multiple proteins from a single gene. It is also associated with a growing number of human diseases.

SMA is an often-fatal genetic disorder resulting from the loss of the SMN protein encoded by the Survival Motor Neuron SMN gene. The SMN genes, SMN1 and SMN2, are located on chromosome 5 and SMA is caused by the loss of SMN1 from both chromosomes. SMN2, while being almost identical to SMN1, is less effective at making the SMN protein. The severity of SMA is affected by the efficiency at which SMN2, of which there are several copies, produces the SMN protein.

SMN1 encodes a ubiquitously expressed 38 kDa SMN protein that is necessary for snRNP assembly, an essential process for cell survival. A nearly identical copy of the gene, SMN2, fails to compensate for the loss of SMN1 because of exon 7 skipping, producing an unstable truncated protein, SMNΔ7. SMN1 and SMN2 differ by a critical C to T substitution at position 6 of exon 7 (C6U in transcript of SMN2). C6U does not change the coding sequence, but is sufficient to cause exon 7 skipping in SMN2.

Current treatment for SMA consists of prevention and management of the secondary effect of chronic motor unit loss. Currently, there are no drug therapies available for the treatment or prevention of SMA.

Antisense technology, used mostly for RNA downregulation, recently has been adapted to alter the splicing process. Effective agents that can alter splicing of SMN2 pre-mRNAs are likely to be useful therapeutically.

SUMMARY OF THE INVENTION

The present application relates to methods of enhancing the level of exon 7-containing SMN2 mRNA relative to exon-deleted SMN2 mRNA in a cell, comprising contacting the cell with an antisense oligonucleotide of sufficient length and complementarity to specifically hybridize to a region within the SMN2 gene, such that the level of exon 7-containing SMN2 mRNA relative to exon-deleted SMN2 mRNA in the cell is enhanced, wherein the antisense oligonucleotide has at least one nucleoside that is positively charged at physiological pH.

In one embodiment, the antisense oligonucleotide has at least one internucleoside linkage that exhibits a pKa between about 4.5 and about 12. Preferably, the antisense oligonucleotide has an internucleoside linkage containing both a basic nitrogen and an alkyl, aryl, or aralkyl group. In other embodiments the antisense oligonucleotide comprises a morpholino.

In other embodiments the antisense oligonucleotide includes at least one nucleotide having a formula:

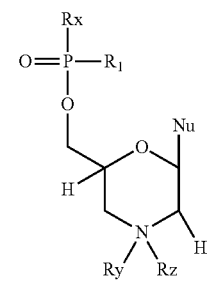

wherein Nu is a nucleobase;
$R_1$ is a moiety of the formula

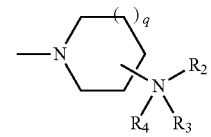

q is 0, 1, 2, 3 or 4;
$R_2$ is selected from the group consisting of hydrogen, $C_1$-$C_5$ alkyl, and a formamidinyl moiety, and
$R_3$ is selected from the group consisting of hydrogen and $C_1$-$C_5$ alkyl, or
$R_2$ and $R_3$ are joined to form a 5-7 membered heterocyclic ring optionally containing an oxygen hetero atom, where the ring may be optionally substituted with a substituent selected from the group consisting of $C_1$-$C_5$ alkyl, phenyl, halogen, and aralkyl;
$R_4$ is selected from the group consisting of null, hydrogen, a $C_1$-$C_6$ alkyl and aralkyl;
$R_x$ is selected from the group consisting of HO—, a nucleotide, a cell penetrating peptide moiety, and piperazinyl;
$R_y$ is selected from the group consisting of hydrogen, a $C_1$-$C_6$ alkyl, a nucleotide, a peptide moiety, an amino acid, a formamidinyl moiety, and acyl; and,
$R_z$ is selected from the group consisting of null, hydrogen, a $C_1$-$C_6$ alkyl, and acyl;
and pharmaceutically acceptable salts thereof.
Preferably, Nu is selected from the group consisting of adenine, guanine, thymine, uracil, cytosine, and hypoxanthine.

Other methods of enhancing the level of exon 7-containing SMN2 mRNA relative to exon-deleted SMN2 mRNA in a cell, comprise contacting the cell with an antisense oligonucleotide of sufficient length and complementarity to specifically hybridize to a region within the SMN2 gene, such that the level of exon 7-containing SMN2 mRNA relative to exon-deleted SMN2 mRNA in the cell is enhanced, wherein the antisense oligonucleotide has at least one nucleoside that has the formula:

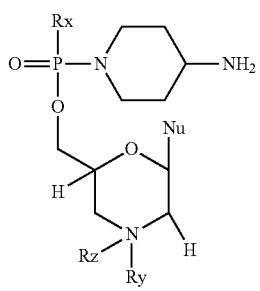

wherein Rx, Ry, Rz, and Nu are as stated above.

In another embodiment, methods of enhancing the level of exon 7-containing SMN2 mRNA relative to exon-deleted SMN2 mRNA in a cell include contacting the cell with an antisense oligonucleotide of sufficient length and complementarity to specifically hybridize to a region within the SMN2 gene, such as a region within exon 7, intron 7, or exon 8 (or a region which spans a splice junction) of the SMN2 gene, thereby enhancing the level of exon 7-containing SMN2 mRNA relative to exon-deleted SMN2 mRNA in the cell. Preferably, the antisense oligonucleotide comprises a sequence which is complementary to intron 7 of the SMN2 gene or complementary to exon 8 of the SMN2 gene. Another embodiment relates to antisense oligonucleotides that further comprises a peptide moiety which enhances cellular uptake.

In one embodiment, the antisense oligonucleotide is uncharged. In additional embodiments, the antisense oligonucleotide is charged. For example, one or more internucleotide linkages in the antisense oligonucleotide may have an APN modification. The modified oligonucleotides contain nucleobases T, A, C, G, U or an analog thereof. Preferably the modified internucleotide linkage is derived from a T, C or A subunit.

The invention also pertains to antisense oligonucleotides set forth in Table 1 having an APN modification and use thereof in the methods of the invention.

Methods of treating spinal muscular atrophy (SMA) in a patient are also within the scope of the invention. Such methods include administering to the patient an antisense oligonucleotide comprising a nucleotide sequence of sufficient length and complementarity to specifically hybridize to a region within the SMN2 gene, such that the level of exon 7-containing SMN2 mRNA relative to exon-deleted SMN2 mRNA in the cell is enhanced, wherein the antisense oligonucleotide has at least one nucleoside that is positively charged at physiological pH, thereby treating the patient.

BRIEF DESCRIPTION OF THE FIGURES

FIG. 5: Spinal Muscular Atrophy (SMA) Sequences Tested. Oligonucleotides containing the sequences described above and tested in FIG. 6 contain a PMO backbone with an APN modification at the bold and underlined T bases (4 total modifications for each APN-containing oligo).

DETAILED DESCRIPTION

Figure 1:
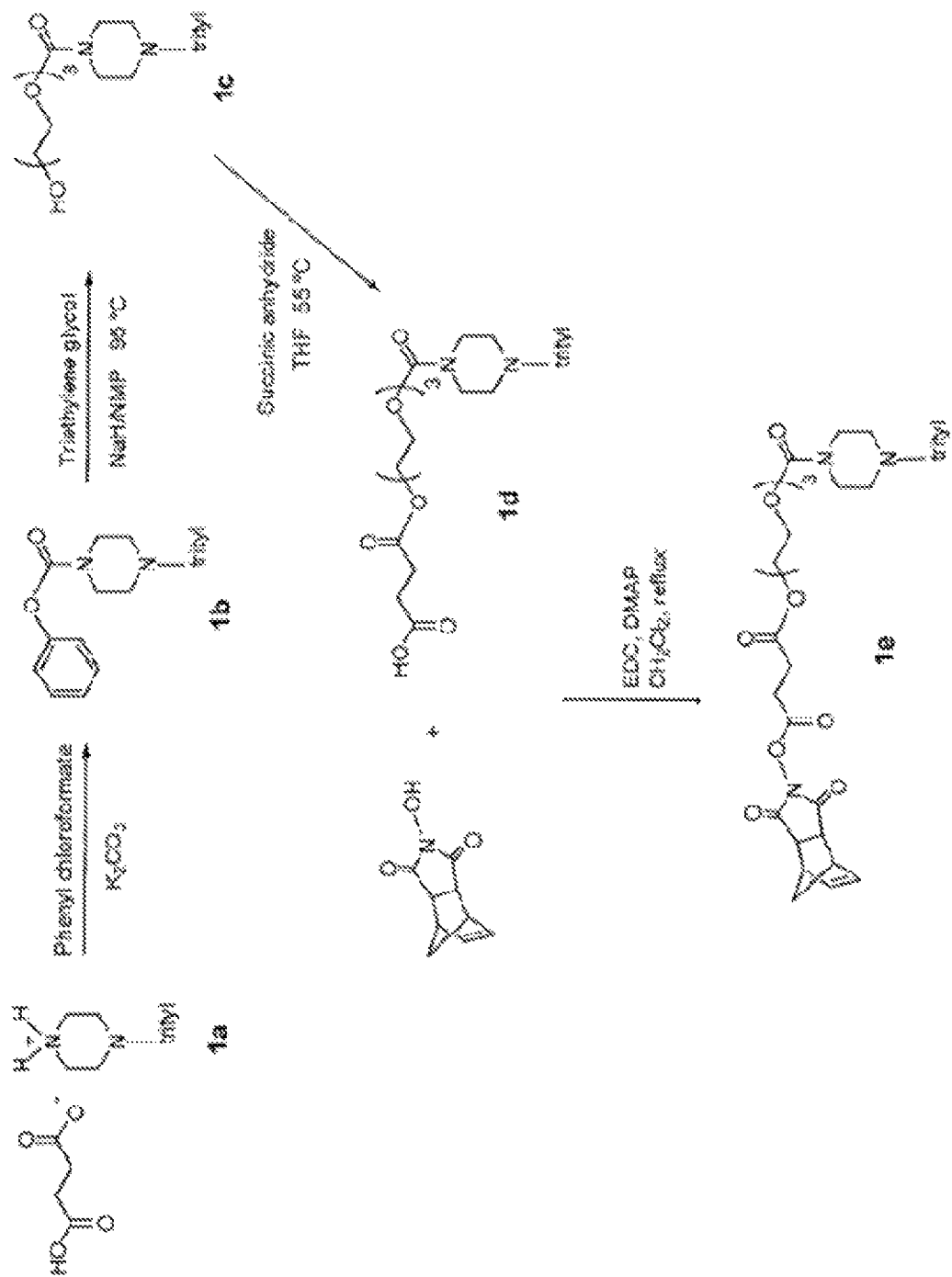
FIGS. 1 and 2: Preparation of the solid support for synthesis of morpholino oligomers.

As used herein, "nucleobase" (Nu), "base pairing moiety" or "base" are used interchangeably to refer to a purine or pyrimidine base found in native DNA or RNA (uracil, thymine, adenine, cytosine, and guanine), as well as analogs of the naturally occurring purines and pyrimidines, that confer improved properties, such as binding affinity to the oligonucleotide. Exemplary analogs include hypoxanthine (the base component of the nucleoside inosine); 5-methyl cytosine; C5-propynyl-modified pyrimidines, 9-(aminoethoxy)phenoxazine (G-clamp) and the like.

Further examples of base pairing moieties include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, RNA, 2003, 9, 1034-1048, Limbach et al. Nucleic Acids Research, 1994, 22, 2183-2196 and Revankar and Rao, Comprehensive Natural Products Chemistry, vol. 7, 313, are also contemplated.

Further examples of base pairing moieties include, but are not limited to, expanded-size nucleobases in which one or more benzene rings has been added. Nucleic base replacements described in the Glen Research catalog (www.glenresearch.com); Krueger A T et al, Acc. Chem. Res., 2007, 40, 141-150; Kool, E T, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, are contemplated as useful for the synthesis of the oligomers described herein. Some examples of these expanded-size nucleobases are shown below:

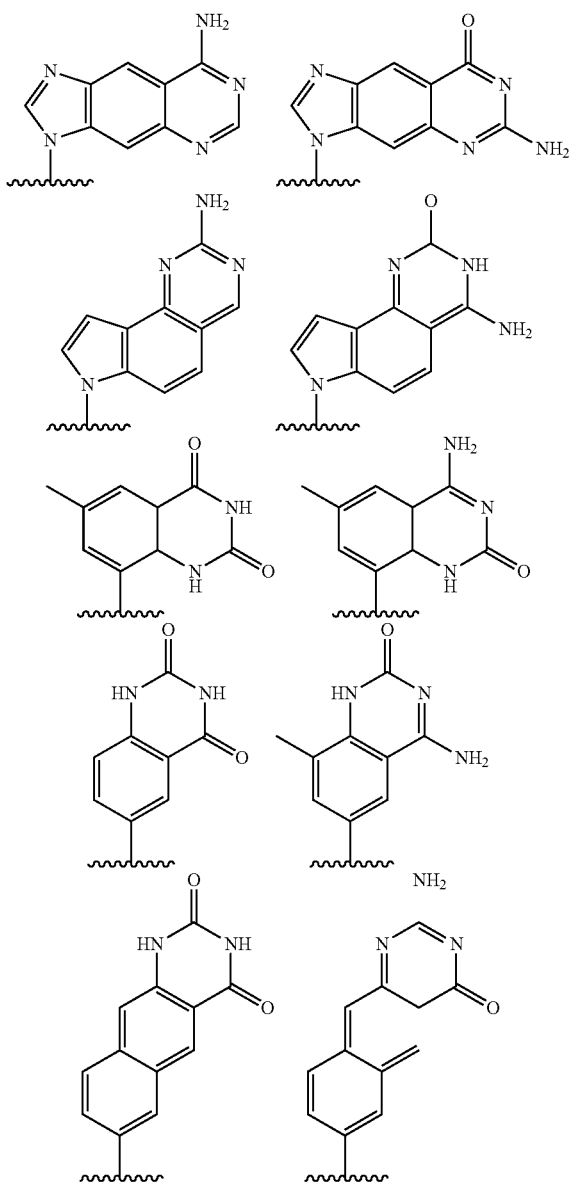

A nucleobase covalently linked to a ribose, sugar analog or morpholino comprises a nucleoside. "Nucleotides" are composed of a nucleoside together with one phosphate group. The phosphate groups covalently link adjacent nucleotides to one another to form an oligonucleotide. As used herein, an "oligonucleotide" is a linear sequence of nucleotides, or nucleotide analogs, that allows the nucleobase to hybridize to a target sequence in an RNA by Watson-Crick base pairing, to form an oligonucleotide:RNA heteroduplex within the target sequence. The terms "antisense oligonucleotide", "antisense oligomer", "oligomer" and "compound" may be used interchangeably to refer to an oligonucleotide.

A "morpholino oligomer" or "PMO" refers to an oligonucleotide having a backbone which supports a nucleobase capable of hydrogen bonding to typical polynucleotides, wherein the polymer lacks a pentose sugar backbone moiety, but instead contains a morpholino ring. Thus, in a PMO a morpholino ring structure supports a base pairing moiety, to form a sequence of base pairing moieties which is typically designed to hybridize to a selected antisense target in a cell or in a subject being treated. An exemplary "morpholino" oligomer comprises morpholino subunit structures linked together by phosphoramidate or phosphorodiamidate linkages, joining the morpholino nitrogen of one subunit to the 4' exocyclic carbon of an adjacent subunit, each subunit comprising a purine or pyrimidine nucleobase effective to bind, by base-specific hydrogen bonding, to a base in a polynucleotide. Morpholino oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT publication number WO/2009/064471 all of which are incorporated herein by reference in their entirety.

Within the oligonucleotide structure, the phosphate groups are commonly referred to as forming the "internucleoside linkages" of the oligonucleotide. The naturally occurring internucleoside linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the cationic intersubunit linkages of the PMO and/or PMOX oligomers described herein, one nitrogen is always pendant to the backbone chain. The second nitrogen, in a phosphorodiamidate linkage, is typically the ring nitrogen in a morpholino ring structure.

"PMOX" refers to phosphorodiamidate morpholino oligomers having a phosphorus atom with (i) a covalent bond to the nitrogen atom of a morpholino ring and (ii) a second covalent bond to the ring nitrogen of a 4-aminopiperidin-1-yl (i.e. APN) or a derivative of 4-aminopiperidin-1-yl. PMOX oligomers are disclosed in PCT application No. PCT/US11/38459 (published as WO/2011/150408), herein incorporated by reference in its entirety. "PMOapn" or "APN" refers to a PMOX oligomer where a phosphorus atom is linked to a morpholino group and to the ring nitrogen of a 4-aminopiperidin-1-yl (i.e. APN).

As used herein, LNA refers to locked nucleic acid oligonucleotides. "LNA" are a member of a class of modifications called bridged nucleic acid (BNA). BNA is characterized by a covalent linkage that locks the conformation of the ribose ring in a C30-endo (northern) sugar pucker. For LNA, the bridge is composed of a methylene between the 2'-O and the 4'-C positions. LNA enhances backbone preorganization and base stacking to increase hybridization and thermal stability.

An oligonucleotide "specifically hybridizes" to a target polynucleotide if the oligomer hybridizes to the target under physiological conditions, with a Tm substantially greater than 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Such hybridization may occur with "near" or "substantial" complementarity of the antisense oligomer to the target sequence, as well as with exact complementarity.

A targeting sequence may have "near" or "substantial" complementarity to the target sequence and still function for the purpose of the present invention, that is, still be "complementary." Preferably, the oligonucleotide analog compounds employed in the present invention have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein.

"An electron pair" refers to a valence pair of electrons that are not bonded or shared with other atoms.

The terms "cell penetrating peptide" (CPP) or "a peptide moiety which enhances cellular uptake" are used interchangeably and refer to cationic cell penetrating peptides, also called "transport peptides", "carrier peptides", or "peptide transduction domains". The peptides, as shown herein, have the capability of inducing cell penetration within 30%, 40%, 50%, 60%, 70%, 80%, 90% or 100% of cells of a given cell culture population, including all integers in between, and allow macromolecular translocation within multiple tissues in vivo upon systemic administration. In one embodiment, the cell-penetrating peptide may be an arginine-rich peptide transporter. In another embodiment, the cell-penetrating peptide may be Penetratin or the Tat peptide. These peptides are well known in the art and are disclosed, for example in US Publication No. 2010-0016215 A1, incorporated by reference in its entirety. A particularly preferred approach to conjugation of peptides to antisense oligonucleotides can be found in PCT publication WO2012/150960 which is incorporated by reference in its entirety. A preferred embodiment of a peptide conjugated oligo utilizes glycine as the linker between the CPP and the antisense oligonucleotide. For example, antisense oligonucleotides of the invention can be coupled to an arginine-rich peptide, such as (Arg)$_6$Gly (6 arginine and 1 glycine linked to an oligonucleotide); e.g., a preferred peptide conjugated PMO consists of R6-G-PMO.

By "isolated" is meant material that is substantially or essentially free from components that normally accompany it in its native state. For example, an "isolated polynucleotide" or "isolated oligonucleotide," as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

As used herein, "sufficient length" refers to an antisense oligonucleotide that is complementary to at least 8, more typically 8-40, contiguous nucleobases in the RNA. An antisense oligonucleotide of sufficient length has at least a minimal number of nucleotides to be capable of specifically hybridizing to the RNA. Preferably an oligonucleotide of sufficient length is from 10 to 40 nucleotides in length, including oligonucleotides of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40 nucleotides. In one embodiment, an oligonucleotide of sufficient length is from 10 to about 30 nucleotides in length. In another embodiment, an oligonucleotide of sufficient length is from 15 to about 25 nucleotides in length. In yet another embodiment, an oligonucleotide of sufficient length is from 20 to about 30 nucleotides in length.

As used herein, the terms "contacting a cell", "introducing" or "delivering" refers to delivery of the oligonucleotides of the invention into a cell by methods routine in the art, e.g., transfection (e.g., liposome, calcium-phosphate, polyethyleneimine), electroporation (e.g., nucleofection), microinjection).

As used herein, the term "quantifying", "quantification" or other related words refer to determining the quantity, mass, or concentration in a unit volume, of a nucleic acid, polynucleotide, oligonucleotide, peptide, polypeptide, or protein.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent.

Structural Features of the Oligonucleotides

As noted above, the substantially uncharged oligonucleotide may be modified, in accordance with an aspect of the invention, to include charged linkages, e.g., up to about 1 per every 2-5 uncharged linkages, such as about 4-5 per every 10 uncharged linkages. In certain embodiments, optimal improvement in antisense activity may be seen when about 25% of the backbone linkages are cationic. In certain embodiments, enhancement may be seen with a small number e.g., 10-20% cationic linkages, or where the number of cationic linkages are in the range 50-80%, such as about 60%.

In certain embodiments, the antisense compounds can be prepared by stepwise solid-phase synthesis, employing methods detailed in the references cited above, and below with respect to the synthesis of oligonucleotides having a mixture or uncharged and cationic backbone linkages. In some cases, it may be desirable to add additional chemical moieties to the antisense compound, e.g., to enhance pharmacokinetics or to facilitate capture or detection of the compound. Such a moiety may be covalently attached, according to standard synthetic methods. For example, addition of a polyethyleneglycol moiety or other hydrophilic polymer, e.g., one having 1-100 monomeric subunits, may be useful in enhancing solubility.

A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense compound, it is generally of course desirable to select chemical compounds of groups that are biocompatible and likely to be tolerated by a subject without undesirable side effects.

As noted above, certain of the antisense compounds can be constructed to contain a selected number of cationic linkages interspersed with uncharged linkages of the type described above. The intersubunit linkages, both uncharged and cationic, preferably are phosphorus-containing linkages, having the structure:

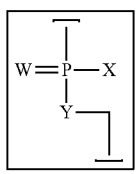

where
W is S or O, and is preferably O,
X=$R_1$, $NR^{11}R^{12}$ or $OR^{16}$,
Y=O or $NR^{17}$,
and each said linkage in the oligomer is selected from:
(a) uncharged linkage (a), where each of $R^{11}$, $R^{12}$, $R^{16}$ and $R^{17}$ is independently selected from hydrogen and $C_1$-$C_6$ alkyl; or
(b1) cationic linkage (1), where $R_1$ is a moiety of the formula

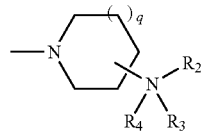

q is 0, 1, 2, 3 or 4;
$R_2$ is selected from the group consisting of hydrogen, $C_1$-$C_5$ alkyl, and a formamidinyl moiety, and
$R_3$ is selected from the group consisting of hydrogen and $C_1$-$C_5$ alkyl, or
$R_2$ and $R_3$ are joined to form a 5-7 membered heterocyclic ring optionally containing an oxygen heteroatom, where the ring may be optionally substituted with a substituent selected from the group consisting of $C_1$-$C_5$ alkyl, phenyl, halogen, and aralkyl;
$R_4$ is selected from the group consisting of null, hydrogen, $C_1$-$C_6$ alkyl and aralkyl;
(b2) cationic linkage (b2), where X=$NR^{11}R^{12}$ and Y=O, and $NR^{11}R^{12}$ represents an optionally substituted piperazino group of the formula

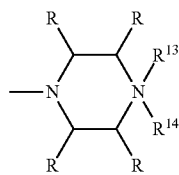

where
each R is independently H or $CH_3$,
$R^{14}$ is H, $CH_3$, or null, and
$R^{13}$ is selected from H, $C_1$-$C_6$ alkyl, 5-7 membered substituted or unsubstituted aryl, heteroaryl or heterocyclic ring containing up to 2 heteroatoms selected from the groups consisting of N and O, C(=NH)$NH_2$, Z-L-NRR, Z-L-NHC(=NH)$NH_2$, Z-L-COOH, Z-L-SH, Z-L-$PPh_3$, Z-L-$R^{21}$—$R^{22}$, cholate, and [C(O)CHR'NH]$_m$H, where: Z is C(O) or a direct bond, L is an optional linker up to 18 atoms in length, preferably up to 12 atoms, and more preferably up to 8 atoms in length, having bonds selected from alkyl, alkoxy, and alkylamino, R' is a side chain of a naturally occurring amino acid or a one- or two-carbon homolog thereof, m is 1 to 6, preferably 1 to 4; $R^{21}$ is a 5-7 membered aryl ring, and $R^{22}$ is a 5-7 membered heteroaryl ring containing up to 4 heteroatoms selected from the groups consisting of N and O;

(b3) cationic linkage (b3), where X=$NR^{11}R^{12}$ and Y=O, $R^{11}$=H or $CH_3$, and $R^{12}$=$LNR^{13}R^{14}R^{15}$, where L, $R^{13}$, and $R^{14}$ are as defined above, and $R^{15}$ is H, $C_1$-$C_6$ alkyl, or $C_1$-$C_6$ (alkoxy)alkyl; and (b4) cationic linkage (b4), where Y=$NR^{17}$ and X=$OR^{16}$, and $R^{17}$=$LNR^{13}R^{14}R^{15}$, where L, $R^{13}$, $R^{14}$ and $R^{15}$ are as defined above, and $R^{16}$ is H or $C_1$-$C_6$ alkyl;

and at least one said linkage is selected from cationic linkages (b1), (b2), (b3) and (b4).

In certain embodiments, an oligomer may include at least two consecutive linkages of type (a) (i.e. uncharged linkages). In further embodiments, at least 5% of the linkages in the oligomer are cationic linkages (i.e. type (b1), (b2), (b3) or (b4)); for example, 10% to 60%, and preferably 20-50% linkages may be cationic linkages.

In one embodiment, at least one linkage is of the type (b1), where, q is 1, $R_2$ and $R_3$ are hydrogen and $R_4$ is null.

In one embodiment, at least one linkage is of type (b2), where, preferably, each R is H, $R^{14}$ is H, $CH_3$, or null, and $R^{13}$ is selected from H, $C_1$-$C_6$ alkyl, C(=NH)$NH_2$, and C(O)-L-NHC(=NH)$NH_2$. The latter two embodiments of $R^{13}$ provide a guanidinyl moiety, either attached directly to the piperazine ring, or pendant to a linker group L, respectively. For ease of synthesis, the variable Z in $R^{13}$ is preferably C(O) (carbonyl), as shown.

The linker group L, as noted above, contains bonds in its backbone selected from alkyl (e.g., —$CH_2$—$CH_2$—), alkoxy (—C—O—), and alkylamino (e.g., —$CH_2$—NH—), with the proviso that the terminal atoms in L (e.g., those adjacent to carbonyl or nitrogen) are carbon atoms. Although branched linkages (e.g., —$CH_2$—$CHCH_3$—) are possible, the linker is preferably unbranched. In one embodiment, the linker is a hydrocarbon linker. Such a linker may have the structure —$(CH_2)_n$—, where n is 1-12, preferably 2-8, and more preferably 2-6.

The morpholino subunits (nucleotide) have the structure:

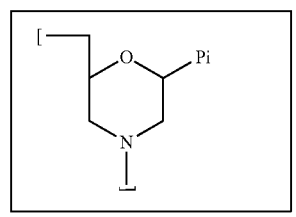

(i)

where Pi is a base-pairing moiety, and the linkages depicted above connect the nitrogen atom of (i) to the 5' carbon of an adjacent subunit. The base-pairing moieties Pi may be the same or different, and are generally designed to provide a sequence which binds to a target nucleic acid.

The use of embodiments of linkage types (b1), (b2) (b3) and (b4) above to link morpholino subunits may be illustrated graphically as follows:

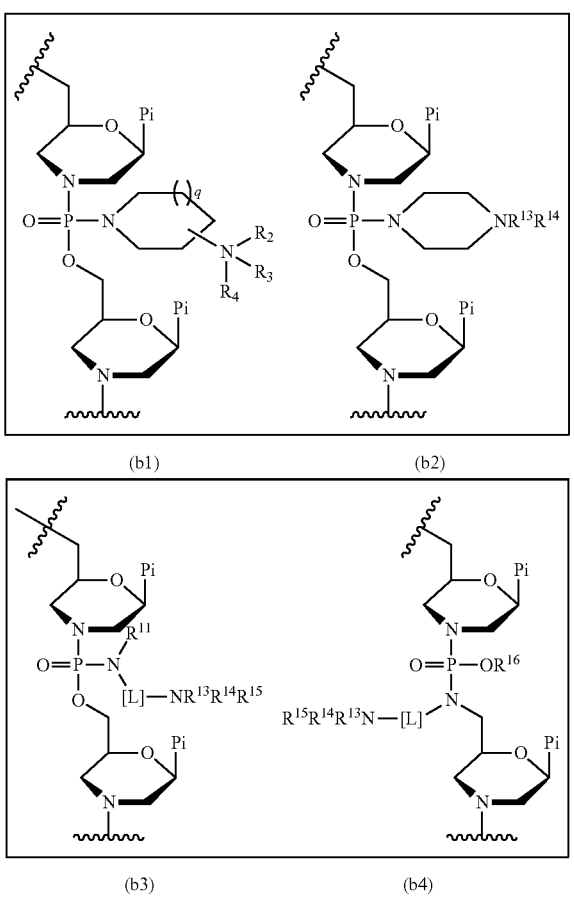

(b1)  (b2)  (b3)  (b4)

Preferably, but not necessarily, all cationic linkages in the oligomer are of the same type; i.e. all of type (b1), all of type (b2), all of type (b3) or all of type (b4).

In further embodiments, the cationic linkages are selected from linkages (b2') and (b2") as shown below, where (b2') is referred to herein as a "Pip" linkage and (b2") is referred to herein as a "GuX" linkage:

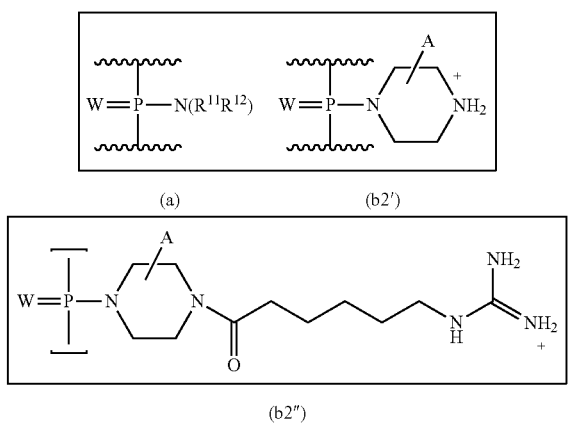

(a)  (b2')

(b2")

In the structures above, W is S or O, and is preferably O; each of $R^{11}$ and $R^{12}$ is independently selected from hydrogen and $C_1$-$C_6$ alkyl, and is preferably methyl or ethyl; and A represents hydrogen or $C_1$-$C_6$ alkyl on one or more carbon atoms in (b2') and (b2"). Preferably, the ring carbons in the piperazine ring are unsubstituted; however, they may include non-interfering substituents, such as methyl. Preferably, at most one or two carbon atoms is so substituted. In further embodiments, at least 10% of the linkages are of type (b2') or (b2"); for example, 10%-60% and preferably 20% to 50%, of the linkages may be of type (b2') or (b2").

In certain embodiments, the oligomer contains no linkages of the type (b2') above. Alternatively, the oligomer contains no linkages of type (b2) where each R is H, $R^{13}$ is H or $CH_3$, and $R^{14}$ is H, $CH_3$, or null.

The morpholino subunits may also be linked by non-phosphorus-based intersubunit linkages, as described further below, where at least one linkage is modified with a pendant cationic group as described above.

Other oligonucleotide analog linkages which are uncharged in their unmodified state but which could also bear a pendant amine substituent could be used. For example, a 5'-nitrogen atom on a morpholino ring could be employed in a sulfamide linkage or a urea linkage (where phosphorus is replaced with carbon or sulfur, respectively) and modified in a manner analogous to the 5'-nitrogen atom in structure (b4) above.

Oligomers having any number of cationic linkages are provided, including fully cationic-linked oligomers. Preferably, however, the oligomers are partially charged, having, for example, 10%-80%. In preferred embodiments, about 10% to 60%, and preferably 20% to 50% of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5', 3' and center regions, and the percentage of cationic linkages in the center region is greater than about 50%, preferably greater than about 70%.

Oligomers for use in antisense applications generally range in length from about 10 to about 40 subunits, more preferably about 10 to 30 subunits, and typically 15-25 bases. For example, an oligomer of the invention having 19-20 subunits, a useful length for an antisense compound, may ideally have two to ten, e.g., four to eight, cationic linkages, and the remainder uncharged linkages. An oligomer having 14-15 subunits may ideally have two to seven, e.g., 3, 4, or 5, cationic linkages and the remainder uncharged linkages.

Each morpholino ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (e.g., A, G, C, T or U) or an analog, such as hypoxanthine (the base component of the nucleoside inosine) or 5-methyl cytosine.

As noted above, certain embodiments are directed to oligomers comprising novel intersubunit linkages, including PMO-X oligomers and those having modified terminal groups. In some embodiments, these oligomers have higher affinity for DNA and RNA than do the corresponding unmodified oligomers and demonstrate improved cell delivery, potency, and/or tissue distribution properties compared to oligomers having other intersubunit linkages. In one embodiment, the oligomers comprise at least one intersubunit linkage of type (B) as defined herein. The oligomers may also comprise one or more intersubunit linkages of type (A) as defined herein. The structural features and properties of the various linkage types and oligomers are described in more detail in the following discussion. The synthesis of these and related oligomers is described in co-owned U.S. application Ser. No. 13/118,298, which is incorporated by reference in its entirety.

In preferred embodiments, the invention provides for an oligonucleotide having a sequence complementary to the target sequence which is associated with a human disease, and comprises a sequence of nucleotides having a formula:

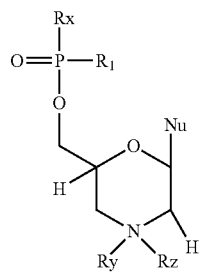

wherein Nu is a nucleobase;
$R_1$ is selected from the group consisting of $R_1'$ and $R_1''$ wherein $R_1'$ is dimethylamino and $R_1''$ is a moiety of the formula

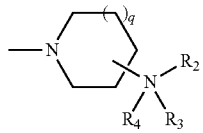

wherein at least one $R_1$ is $R_1''$;
q is 0, 1, 2, 3 or 4;
$R_2$ is selected from the group consisting of hydrogen, $C_1$-$C_5$ alkyl, and a formamidinyl moiety, and
$R_3$ is selected from the group consisting of hydrogen and $C_1$-$C_5$ alkyl, or
$R_2$ and $R_3$ are joined to form a 5-7 membered heterocyclic ring optionally containing an oxygen hetero atom, where the ring may be optionally substituted with a substituent selected from the group consisting of $C_1$-$C_5$ alkyl, phenyl, halogen, and aralkyl;
$R_4$ is selected from the group consisting of null, hydrogen, a $C_1$-$C_6$ alkyl and aralkyl;
Rx is selected from the group consisting of HO—, a nucleotide, a cell penetrating peptide moiety, and piperazinyl;
Ry is selected from the group consisting of hydrogen, a $C_1$-$C_6$ alkyl, a nucleotide, a peptide moiety, an amino acid, a formamidinyl moiety, and acyl; and,
Rz is selected from the group consisting of an null, hydrogen, a $C_1$-$C_6$ alkyl, and acyl; and pharmaceutically acceptable salts thereof.

Nu may be selected from the group consisting of adenine, guanine, thymine, uracil, cytosine, and hypoxanthine. More preferably Nu is thymine or uracil.

About 50-90% of the $R_1$ groups are dimethylamino (i.e., $R_1'$). Most, preferably about 66% (two thirds) of the $R_1$ groups are dimethylamino.

$R_1$ may be selected from the group consisting of

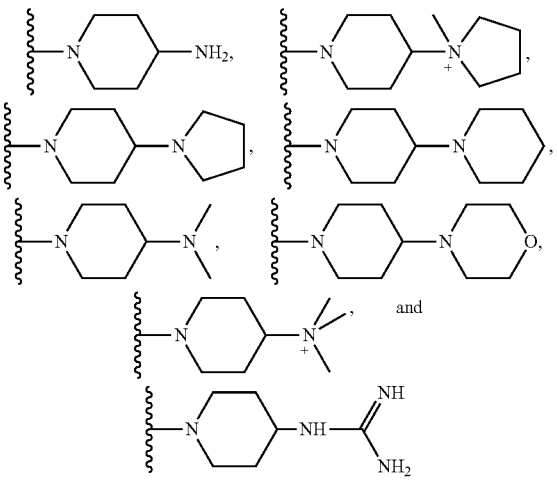

Preferably, at least one nucleotide of the oligonucleotide has the formula:

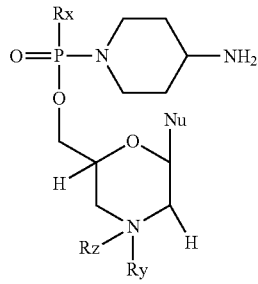

wherein Rx, Ry, Rz, and Nu are as stated above. Most preferably, Nu is thymine or uracil.

Although thymine (T) is the preferred base pairing moiety (Nu or Pi) containing the chemical modifications described above, any base subunit known to a person of skill in the art can be used as the base pairing moiety.

Antisense Oligonucleotides

The invention provides for the use of an antisense oligonucleotide that comprises a sequence selected from the group set forth in Table 1. Preferably, the antisense oligonucleotide comprises a sequence selected from the group consisting of 14-mer-APN, E-8/4a-APN and E8/4b-APN. Additional antisense oligonucleotides that can be used in accordance with the present invention include those described in the following patents and patent publications, the contents of which are incorporated herein by reference: WO2007/002390 WO2010/120820 WO2010/148249 U.S. Pat. No. 7,838,657 US 2011/0269820

The invention further relates to the antisense oligonucleotides set forth in Table 1 having an APN modification or APN derivative. Particular antisense oligonucleotides useful in the methods described herein include 14-mer-APN, E-8/4a-APN and E8/4b-APN.

As used herein, the term "antisense oligonucleotide" refers to a nucleic acid (in preferred embodiments, an RNA) (or analog thereof), having sufficient sequence complementarity to a target RNA (i.e., the RNA for which splice site selection is modulated) to block a region of a target RNA (e.g., pre-mRNA) in an effective manner. In exemplary embodiments of the instant invention, such blocking of SMN2 pre-mRNA serves to modulate splicing, either by masking a binding site for a native protein that would otherwise modulate splicing and/or by altering the structure of the targeted RNA. In preferred embodiments of the instant invention, the target RNA is target pre-mRNA (e.g., SMN2 pre-mRNA). An antisense oligonucleotide having a sufficient sequence complementarity to a target RNA sequence to modulate splicing of the target RNA means that the antisense agent has a sequence sufficient to trigger the masking of a binding site for a native protein that would otherwise modulate splicing and/or alters the three-dimensional structure of the targeted RNA. Likewise, an oligonucleotide reagent having a sufficient sequence complementary to a target RNA sequence to modulate splicing of the target RNA means that the oligonucleotide reagent has a sequence sufficient to trigger the masking of a binding site for a native protein that would otherwise modulate splicing and/or alters the three-dimensional structure of the targeted RNA.

In some embodiments, the antisense oligonucleotide is uncharged. In additional embodiments, the antisense oligonucleotide is charged.

In some embodiments, the antisense oligonucleotide may be a "morpholino oligomer," "PMO," "PMOX," "PPMO," or "PMO+". Furthermore, the antisense oligonucleotide, e.g., PMO, may be modified in any manner known in the art. One or more internucleotide linkages in the antisense oligonucleotide may be modified. For example, one or more internucleotide linkages in the antisense oligonucleotide may have a cationic modification. The cationic modification may be an APN modification. Preferably the modified internucleotide linkages are derived from a T, C or A subunit. For example, in one embodiment, the PMO may comprise a cationic modification. The PMO may be an APN modified PMO, which may be referred to as a "PMOapn" or "APN."

As used herein, the term "SMA" refers to spinal muscular atrophy, a human autosomal recessive disease that is often characterized by underexpression of SMN protein in affected individuals.

As used herein, the term "target" refers to a RNA region, and specifically, to a region identified by the SMN2 gene. In a particular embodiment the target region is a region of the mRNA of the SMN2 intron 7 region which is responsible for the deletion of exon 7 and is associated with SMN. In another embodiment the target region is a region of the mRNA of SMN2 exon 8.

The term "target sequence" refers to a portion of the target RNA against which the oligonucleotide analog is directed, that is, the sequence to which the oligonucleotide analog will hybridize by Watson-Crick base pairing of a complementary sequence.

The term "targeting sequence" is the sequence in the oligonucleotide analog that is complementary (meaning, in addition, substantially complementary) to the target sequence in the RNA genome. The entire sequence, or only a portion, of the antisense oligonucleotide may be complementary to the target sequence. For example, in an antisense oligonucleotide having 20 bases, only 12-14 may be targeting sequences. Typically, the targeting sequence is formed of contiguous bases in the oligonucleotide, but may alternatively be formed of non-contiguous sequences that when placed together, e.g., from opposite ends of the oligonucleotide, constitute sequence that spans the target sequence.

In general, oligonucleotide reagents containing nucleotide sequences perfectly complementary to a portion of the target RNA are preferred for blocking of the target RNA. However, 100% sequence complementarity between the oligonucleotide reagent and the target RNA is not required to practice the present invention. Thus, the invention may tolerate sequence variations that might be expected due to genetic mutation, strain polymorphism, or evolutionary divergence. For example, oligonucleotide reagent sequences with insertions, deletions, and single point mutations relative to the target sequence may also be effective for inhibition. Alternatively, oligonucleotide reagent sequences with nucleotide analog substitutions or insertions can be effective for blocking.

Greater than 70% sequence identity (or complementarity), e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the oligonucleotide reagent and the target RNA, e.g., target pre-mRNA, is preferred. In addition, variants of the oligonucleotide sequences set forth in Table 1 which retain the function of same can be used in the methods of the invention. For example, a series of mutants may be tested for their ability to inhibit alternative splicing. In one embodiment, such variant sequences are at least about 95% identical in sequence to a sequence set forth in Table 1 over the entire length of the same. In another embodiment, such variant sequences are at least about 90% identical in the sequence over the entire length of the same.

Splice forms and expression levels of surveyed RNAs and proteins may be assessed by any of a wide variety of well known methods for detecting splice forms and/or expression of a transcribed nucleic acid or protein. Non-limiting examples of such methods include RT-PCR of spliced forms of RNA followed by size separation of PCR products, nucleic acid hybridization methods e.g., Northern blots and/or use of nucleic acid arrays; nucleic acid amplification methods; immunological methods for detection of proteins; protein purification methods; and protein function or activity assays.

RNA expression levels can be assessed by preparing mRNA/cDNA (i.e. a transcribed polynucleotide) from a cell, tissue or organism, and by hybridizing the mRNA/cDNA with a reference polynucleotide which is a complement of the assayed nucleic acid, or a fragment thereof. cDNA can, optionally, be amplified using any of a variety of polymerase chain reaction or in vitro transcription methods prior to hybridization with the complementary polynucleotide; preferably, it is not amplified. Expression of one or more transcripts can also be detected using quantitative PCR to assess the level of expression of the transcript(s).

Methods of the Invention

In one aspect, the invention provides for a method for enhancing the level of exon 7-containing SMN2 mRNA relative to exon-7 deleted SMN2 mRNA in a cell, comprising contacting the cell with an antisense oligonucleotide of sufficient length and complementarity to specifically hybridize to a region within the SMN2 gene, such that the level of exon 7-containing SMN2 mRNA relative to exon-7 deleted SMN2 mRNA in the cell is enhanced, wherein the antisense oligonucleotide has at least one internucleoside linkage that is positively charged at physiological pH.

Optionally, the antisense oligonucleotide may have internucleoside linkage with both a basic nitrogen and an alkyl, aryl, or aralkyl group. Preferably, the antisense oligonucleotide comprises a morpholino.

Moreover, the invention provides that the antisense oligonucleotide has at least one internucleoside linkage that is positively charged at physiological pH. The invention also provides that the antisense oligonucleotide has at least one internucleoside linkage that exhibits a pKa between 5.5 and 12.

While not being bound by theory, it is believed that the positively charged APN group or APN derivatives, in the PMOX oligomer facilitates binding to the negatively charged phosphates in target nucleotide. Thus, the formation of a hetroduplex between mutant RNA and the PMOX oligomer may be held together by an ionic attractive force, as well as by Watson-Crick base pairing.

Effective delivery of the antisense oligomer to the target nucleic acid is an important aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. Vascular or extravascular circulation, the blood or lymph system, and the cerebrospinal fluid are some non-limiting sites where the RNA may be introduced.

The antisense oligonucleotides of the invention can be delivered to the nervous system of a subject by any art-recognized method. For example, peripheral blood injection of the antisense oligonucleotides of the invention can be used to deliver said reagents to peripheral neurons via diffusive and/or active means. In one embodiment, the antisense oligonucleotides may be delivered to the brain of the subject. For example, the antisense oligonucleotides may be delivered by intracerebroventriclar (ICV) injection. Alternatively, the antisense oligonucleotides of the invention can be modified to promote crossing of the blood-brain-barrier (BBB) to achieve delivery of said reagents to neuronal cells of the central nervous system (CNS). Specific recent advancements in antisense oligonucleotide technology and delivery strategies have broadened the scope of antisense oligonucleotide usage for neuronal disorders (Forte, A., et al. 2005. Curr. Drug Targets 6:21-29; Jaeger, L. B., and W. A. Banks. 2005. Methods Mol. Med. 106:237-251; Vinogradov, S. V., et al. 2004. Bioconjug. Chem. 5:50-60; the preceding are incorporated herein in their entirety by reference). For example, the antisense oligonucleotides of the invention can be generated as peptide nucleic acid (PNA) compounds. PNA reagents have each been identified to cross the BBB (Jaeger, L. B., and W. A. Banks. 2005. Methods Mol. Med. 106:237-251). Treatment of a subject with, e.g., a vasoactive agent, has also been described to promote transport across the BBB (Id). Tethering of the antisense oligonucleotides of the invention to agents that are actively transported across the BBB may also be used as a delivery mechanism.

In certain embodiments, the antisense oligonucleotides of the invention can be delivered by transdermal methods (e.g., via incorporation of the antisense oligonucleotides into, e.g., emulsions, with such antisense oligonucleotides optionally packaged into liposomes). Such transdermal and emulsion/liposome-mediated methods of delivery are described for delivery of antisense oligonucleotides in the art, e.g., in U.S. Pat. No. 6,965,025, the contents of which are incorporated in their entirety by reference herein.

The antisense oligonucleotides of the invention may also be delivered via an implantable device. Design of such a device is an art-recognized process, with, e.g., synthetic implant design described in, e.g., U.S. Pat. No. 6,969,400, the contents of which are incorporated in their entirety by reference herein.

Antisense oligonucleotides can be introduced into cells using art-recognized techniques (e.g., transfection, electroporation, fusion, liposomes, colloidal polymeric particles and viral and non-viral vectors as well as other means known in the art). The method of delivery selected will depend at least on the cells to be treated and the location of the cells and will be apparent to the skilled artisan. For instance, localization can be achieved by liposomes with specific markers on the surface to direct the liposome, direct injection into tissue containing target cells, specific receptor mediated uptake, viral vectors, or the like.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, inhibit annealing of single strands, stabilize the single strands, or otherwise increase expression of the target gene.

As known in the art, antisense oligonucleotides may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49, incorporated in its entirety herein by reference).

The antisense oligonucleotides may be administered in any convenient vehicle or carrier which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration. "Pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compounds (e.g., antisense oligonucleotides) of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids.

Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" is intended to encompass any and all acceptable salt forms.

In addition, prodrugs are also included within the context of this invention. Prodrugs are any covalently bonded carriers that release a compound in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the antisense oligonucleotides of the invention. Further, in the case of a carboxylic acid (—COOH), esters may be employed, such as methyl esters, ethyl esters, and the like.

In some instances, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., antisense oligonucleotides: a new therapeutic principle, Chemical Reviews, Volume 90, No. 4, 25 pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., J. Biol. Chem. 262:4429-4432, 30 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules.

In one embodiment, the antisense oligonucleotide is administered to a mammalian subject, e.g., human or domestic animal, exhibiting the symptoms of a polynucleotide-repeat disorder, in a suitable pharmaceutical carrier. In one aspect of the method, the subject is a human subject, e.g., a patient diagnosed as having SMA. The patient's condition may also dictate prophylactic administration of an antisense oligonucleotides of the invention, e.g., in the case of a patient who (1) is immunocompromised; (2) is a burn victim; (3) has an indwelling catheter; or (4) is about to undergo or has recently undergone surgery. In one preferred embodiment, the antisense oligonucleotide is contained in a pharmaceutically acceptable carrier, and is delivered orally.

In another preferred embodiment, the oligomer is contained in a pharmaceutically acceptable carrier, and is delivered intravenously (i.v.).

In one embodiment, the antisense compound is administered in an amount and manner effective to result in a peak blood concentration of at least 200-400 nM antisense oligonucleotide. Typically, one or more doses of antisense oligomer are administered, generally at regular intervals, for a period of about one to two weeks. Preferred doses for oral administration are from about 1-1000 mg oligomer per 70 kg. In some cases, doses of greater than 1000 mg oligomer/patient may be necessary. For i.v. administration, preferred doses are from about 0.5 mg to 1000 mg oligomer per 70 kg. The antisense oligomer may be administered at regular intervals for a short time period, e.g., daily for two weeks or less; once every two days; once every three days; once every 3 to 7 days; once every 3 to 10 days; once every 7 to 10 days; once every two weeks; once monthly. However, in some cases the oligomer is administered intermittently over a longer period of time, e.g., for several weeks, months or years. For example, the antisense oligomer may be administered once every two, three, four, five, six, seven, eight, nine, ten, eleven or twelve months. In addition, the antisense oligomer may be administered once every one, two, three, four or five years. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

An effective in vivo treatment regimen using the antisense oligonucleotides of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of disorder under treatment, and corresponding adjustments in the dose or treatment regimen, in order to achieve an optimal therapeutic outcome.

Treatment may be monitored, e.g., by general indicators of disease known in the art. The efficacy of an in vivo administered antisense oligonucleotide of the invention may be determined from biological samples (tissue, blood, urine etc.) taken from a subject prior to, during and subsequent to administration of the antisense oligonucleotide. Assays of such samples include (1) monitoring the presence or absence of heteroduplex formation with target and non-target sequences, using procedures known to those skilled in the art, e.g., an electrophoretic gel mobility assay; (2) monitoring the amount of a mutant mRNA in relation to a reference normal mRNA or protein as determined by standard techniques such as RT-PCR, Northern blotting, ELISA or Western blotting.

In some embodiments, the antisense oligonucleotide is actively taken up by mammalian cells. In further embodiments, the antisense oligonucleotide may be conjugated to a transport moiety (e.g., transport peptide) as described herein to facilitate such uptake.

Methods of Treatment

The invention also relates to methods of increasing expression of exon 7-containing SMN2 mRNA or protein using the antisense oligonucleotides of the present invention for therapeutic purposes (e.g., treating subjects with SMA).

Accordingly, in one embodiment, the present invention provides methods of treating an individual afflicted with SMA.

In one embodiment, cells from a subject having SMA are contacted with an antisense oligonucleotide of the invention to increase expression of exon 7-containing SMN2 mRNA or protein. Exemplary antisense sequences and compositions, such as 14-mer-APN, E-8/4a-APN and E8/4b-APN, are disclosed in Table 1.

In one embodiment, cells from a subject having spinal muscular atrophy are contacted with an oligonucleotide reagent of the invention to inhibit splicing of the SMN2 exon 7. Exemplary oligonucleotide reagents include sequences complementary to intron 7 target sequence or exon 8 target sequence and variants thereof (e.g., as shown herein). In another embodiment, cells from a subject having another disorder that would benefit from inhibition of alternative splicing are contacted with an oligonucleotide reagent of the invention. Target sequences related to the target sequences disclosed herein are present in human intronic sequences. For example, there is a sequence partially homologous to an intron 7 sequence located in intron 10 of human CFTR.

Such agents can also be used in treatment of diseases associated with high susceptibility to oxidative stress such as exposure to Paraquat and induced Parkinson's disease, as well as amyotrophic lateral sclerosis (ALS), another neurological disease characterized by low levels of SMN protein (Veldink, J. H., et al. 2005 Neurology 65(6):820-5).

The antisense oligonucleotides of the invention can be administered to subjects to treat (prophylactically or therapeutically) SMA. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Comparison of APN Modified Oligonucleotides and Unmodified Oligonucleotides

The oligonucleotides of some embodiments of the invention were tested to determine whether an APN modified oligonucleotide would enhance SMN2 Exon 7 inclusion as compared to the unmodified oligonucleotide. The APN modified oligomer referred to as 14-mer-APN (T TTC ATA ATG CTG G) contains APN modifications on the T bases shown in bold (SEQ ID NO:21). The N1 (A TTC ACT TTC ATA ATG CTG G) and the 14mer oligomer (T TTC ATA ATG CTG G) do not contain APN modifications (SEQ ID NOs: 1 and 19, respectively). Similarly, the oligomers referred to as E8/4a-APN(C TAG TAT TTC CTG CAA A TG AG) and E8/4b-APN(C CAG CAT TTC CTG CAA A TG AG) contain APN modifications on the T bases shown in bold (SEQ ID NOs: 43 and 54, respectively); the corresponding oligomers referred to as E8/4a (C TAG TAT TTC CTG CAA ATG AG) and E8/4b (C CAG CAT TTC CTG CAA ATG AG) do not contain APN modifications (SEQ ID NOs: 42 and 53, respectively). See FIG. 5 and Table 1.

Figure 6:
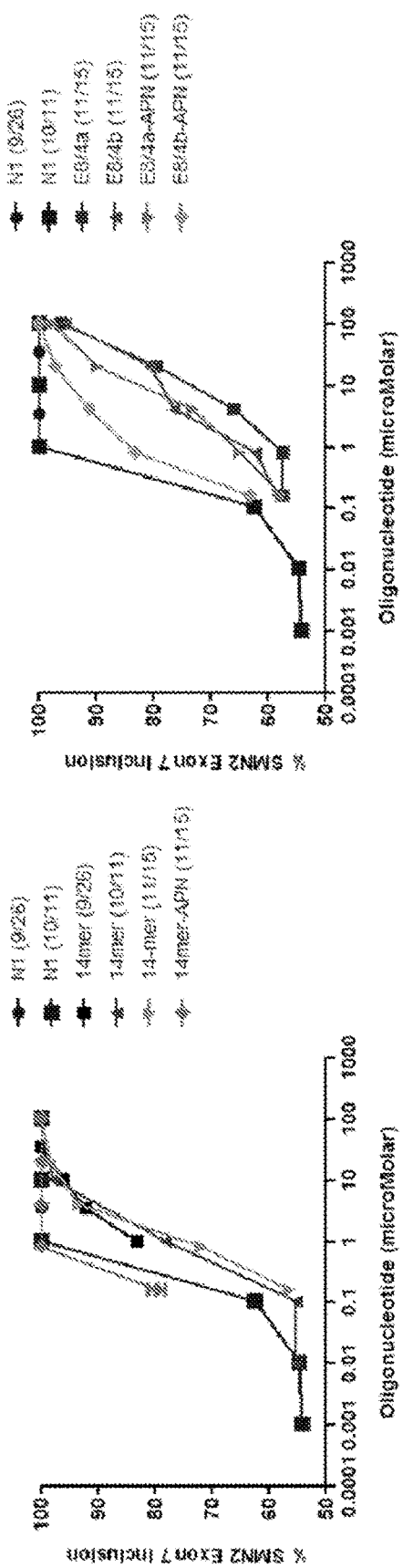
FIG. 6: Dose response curves from oligonucleotide-treated Spinal Muscular Atrophy patient fibroblasts. Intensity of the gel bands representing inclusion or exclusion of SMN2 exon 7 in GM03813 fibroblast cells (Coriell) were quantified with ImageQuant (GE). Exon 7 inclusion is reported as a percentage calculated from the ratio of the exon 7-included band intensities divided by the sum of the intensities from the exon 7-included and -excluded bands. Each dot represents the mean+/−1 standard deviation of two replicates at each concentration. Three independent experiments were combined to yield the above dataset. Percent inclusion analysis was performed in Microsoft Excel. Data points and curves were plotted in Graphpad Prism. The data shows that APN modifications to an oligonucleotide enhances the potency of the compound compared to unmodified PMO containing the same sequence.

It was determined that the addition of APN modifications to an oligonucleotide enhances the potency of the compound compared to unmodified PMO containing the same sequence (See FIG. 6). Specifically, 14 mer (11/15) APN was about an order of magnitude more potent than 14 mer (11/15) without the APN linkage. Likewise E8/4a-APN (11/15) and E8/4b-APN (11/15) were more potent than E8/4a (11/15) and E8/4b (11/15) respectively (See Examples 24 and 25 and FIGS. 6 and 7).

The Preparation of PMO-X with Basic Nitrogen Internucleoside Linkers

Morpholino subunits, the modified intersubunit linkages and oligomers comprising the same can be prepared as described in the examples and in U.S. Pat. Nos. 5,185,444, and 7,943,762 which are hereby incorporated by reference in their entirety. The morpholino subunits can be prepared according to the following general Reaction Scheme I.

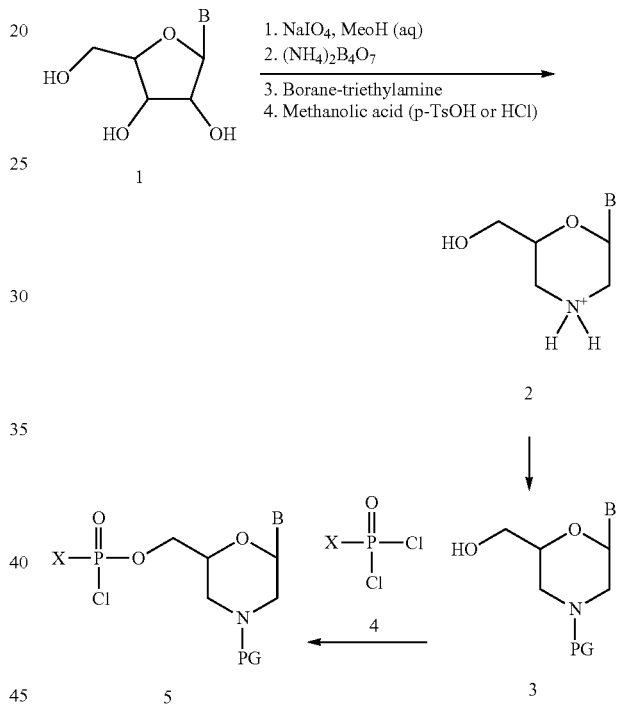

Referring to Reaction Scheme 1, wherein B represents a base pairing moiety and PG represents a protecting group, the morpholino subunits may be prepared from the corresponding ribonucleoside (1) as shown. The morpholino subunit (2) may be optionally protected by reaction with a suitable protecting group precursor, for example trityl chloride. The 3' protecting group is generally removed during solid-state oligomer synthesis as described in more detail below. The base pairing moiety may be suitable protected for sold phase oligomer synthesis. Suitable protecting groups include benzoyl for adenine and cytosine, phenylacetyl for guanine, and pivaloyloxymethyl for hypoxanthine (I). The pivaloyloxymethyl group can be introduced onto the N1 position of the hypoxanthine heterocyclic base. Although an unprotected hypoxanthine subunit, may be employed, yields in activation reactions are far superior when the base is protected. Other suitable protecting groups include those disclosed in co-pending U.S. application Ser. No. 12/271,040, which is hereby incorporated by reference in its entirety.

Reaction of 3 with the activated phosphorous compound 4, results in morpholino subunits having the desired linkage moiety 5. Compounds of structure 4 can be prepared using any number of methods known to those of skill in the art. For example, such compounds may be prepared by reaction of the corresponding amine and phosphorous oxychloride. In this regard, the amine starting material can be prepared using any method known in the art, for example those methods described in the Examples and in U.S. Pat. No. 7,943,762.

Figure 2:
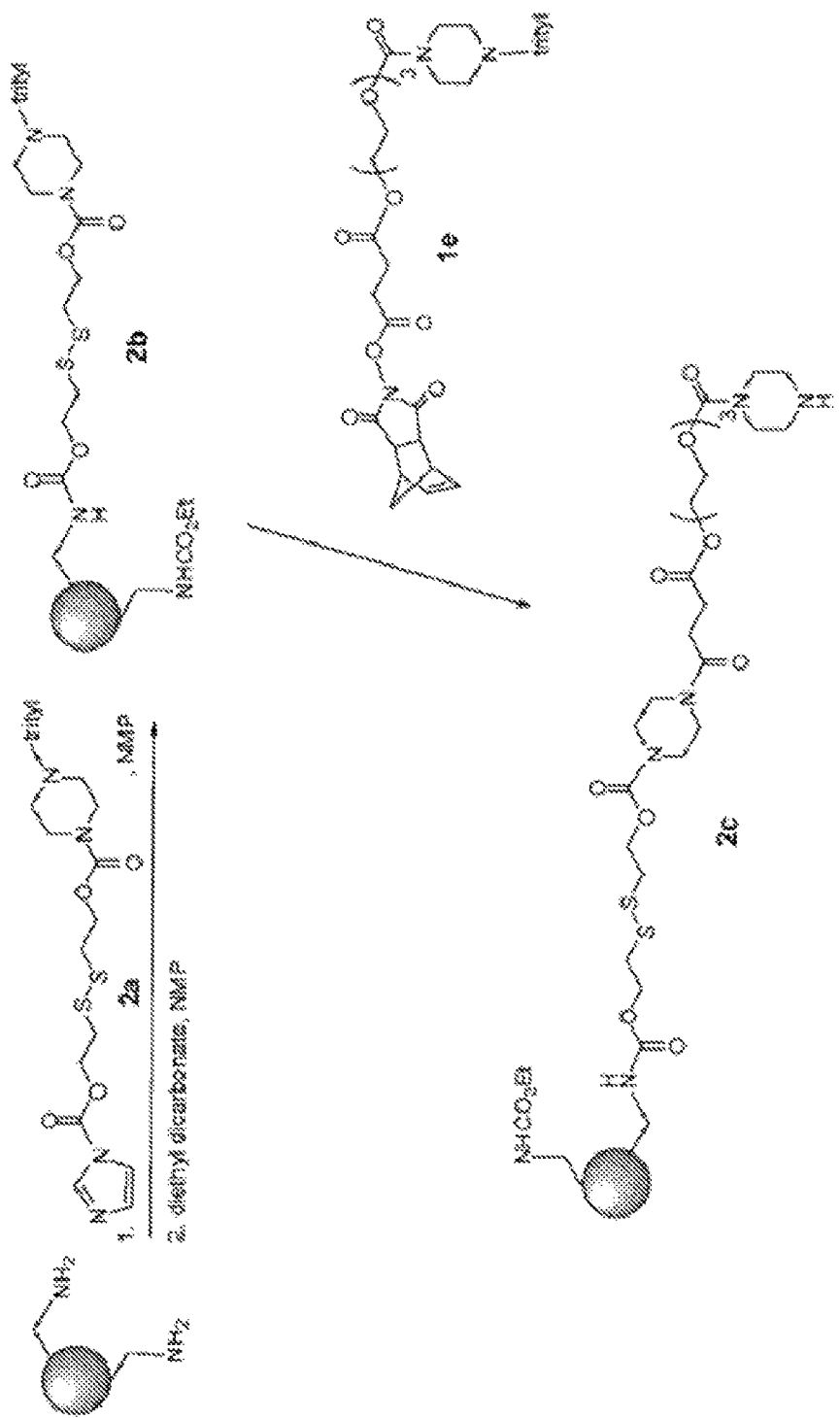
Figure 3:
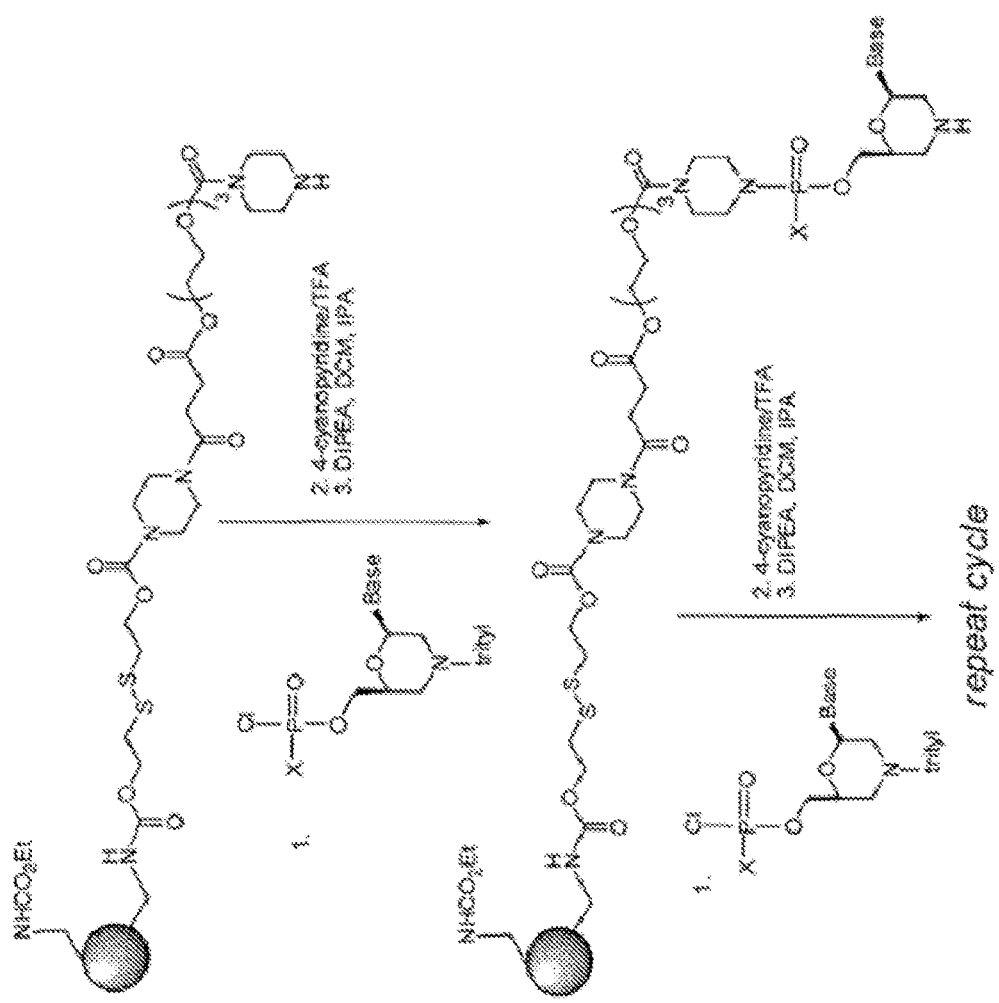
FIGS. 3 and 4: The solid phase synthesis of morpholino oligomers.
Figure 4:
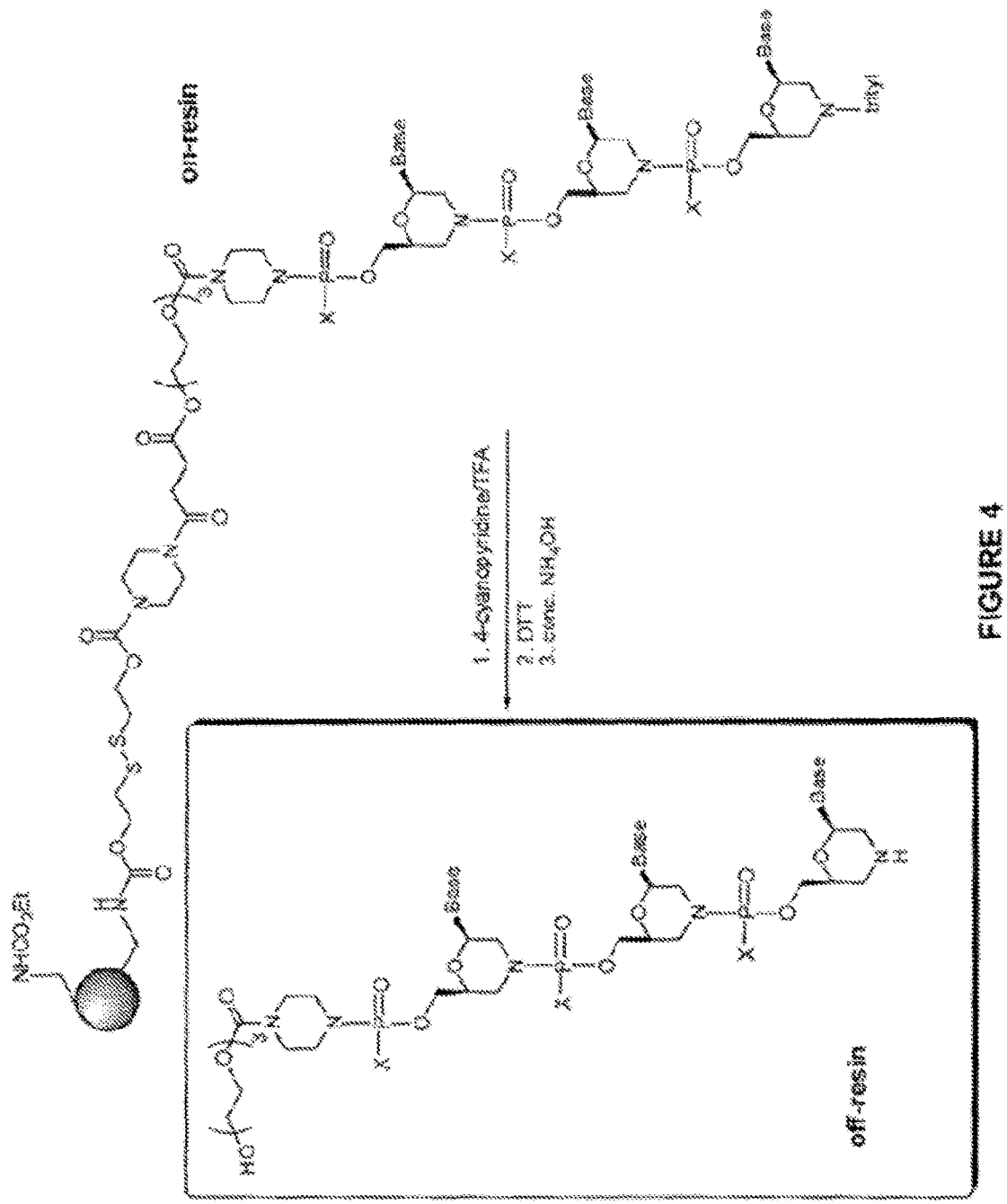

Compounds of structure 5 can be used in solid-phase automated oligomer synthesis for preparation of oligomers comprising the intersubunit linkages. Such methods are well known in the art. Briefly, a compound of structure 5 may be modified at the 5' end to contain a linker to a solid support. For example, compound 5 may be linked to a solid support by a linker comprising $L^{11}$ and $L^{15}$. An exemplary method is demonstrated in FIGS. 1 and 2. Once supported, the protecting group (e.g., trityl) is removed and the free amine is reacted with an activated phosphorous moiety of a second compound of structure 5. This sequence is repeated until the desired length of oligo is obtained. The protecting group in the terminal 5' end may either be removed or left on if a 5'-modification is desired. The oligo can be removed from the solid support using any number of methods, for example treatment with DTT followed by ammonium hydroxide as depicted in FIGS. 3 and 4.

The preparation of modified morpholino subunits and morpholino oligomers are described in more detail in the Examples. The morpholino oligomers containing any number of modified linkages may be prepared using methods described herein, methods known in the art and/or described by reference herein. Also described in the examples are global modifications of morpholino oligomers prepared as previously described (see e.g., PCT publication WO2008036127).

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

Carboxylic acid and hydroxyl reactive moieties may also be blocked with hydrolytically removable protective groups such as the benzyl group, while amine groups may be blocked with base labile groups such as Fmoc. A particularly useful amine protecting group for the synthesis of compounds of Formula (I) is the trifluoroacetamide. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups are known in the art and include, but are not limited to the following moieties:

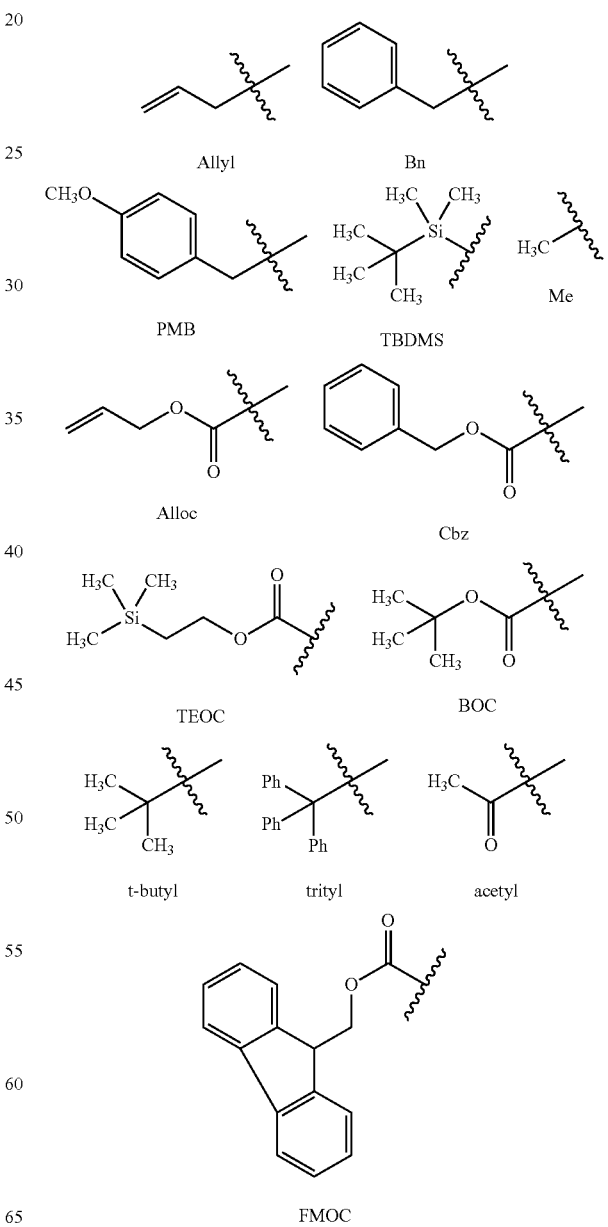

Unless otherwise noted, all chemicals were obtained from Sigma-Aldrich-Fluka. Benzoyl adenosine, benzoyl cytidine, and phenylacetyl guanosine were obtained from Carbosynth Limited, UK.

Synthesis of PMO, PMO+, PPMO, and PMO-X containing further linkage modifications as described herein was done using methods known in the art and described in pending U.S. application Ser. Nos. 12/271,036 and 12/271,040 and PCT publication number WO/2009/064471, which are hereby incorporated by reference in their entirety.

PMO with a 3' trityl modification are synthesized essentially as described in PCT publication number WO/2009/064471 with the exception that the detritylation step is omitted.

Procedure a for the Preparation of Activated Subunits:

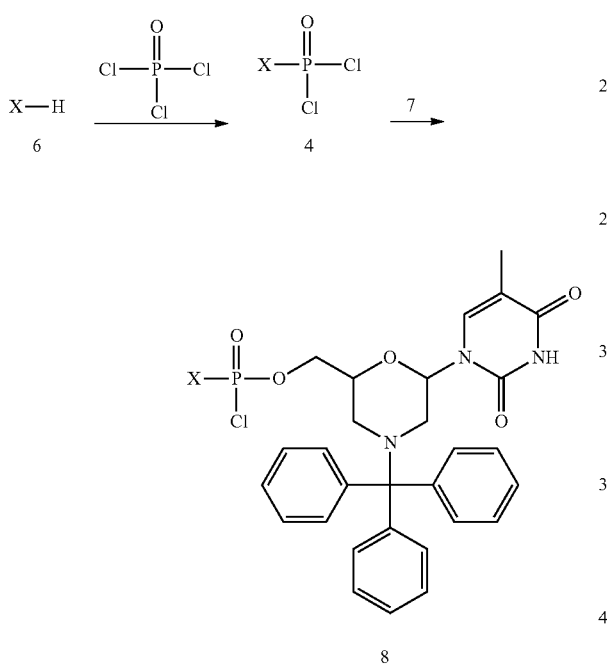

To a stirred solution of 6 (1 eq) in dichloromethane was added $POCl_3$ (1.1 eq), followed by diisopropylethylamine (3 eq) at 0° C., cooled by an ice-bath. After 15 minutes, the ice-bath was removed and the solution was allowed to warm to room temperature for one hour. Upon reaction completion, the reaction solution was diluted with dichloromethane, washed with 10% aqueous citric acid three times. After drying over $MgSO_4$, the organic layer was passed through a plug of silica gel and concentrated in vacuo. The resulting phosphoroamidodichloride (4) was used directly for the next step without further purification.

To a solution of the phosphoroamidodichloride (4) (1 eq), 2,6-lutidine (1 eq) in dichloromethane was added Mo(Tr)T (7) (0.5 eq)/dichloromethane solution, followed by N-methylimidazole (0.2 eq). The reaction stirred at room temperature overnight. Upon reaction completion, the reaction solution was diluted with dichloromethane, and washed with 10% aqueous citric acid three times. After drying over $MgSO_4$, the organic layer was filtered, then concentrated. The product (8) was purified by silica gel chromatography (eluting with a gradient of ethyl acetate/hexanes), and then stored at −20° C. The structure was confirmed by LCMS analysis.

Procedure B for the Preparation of Activated Subunits:

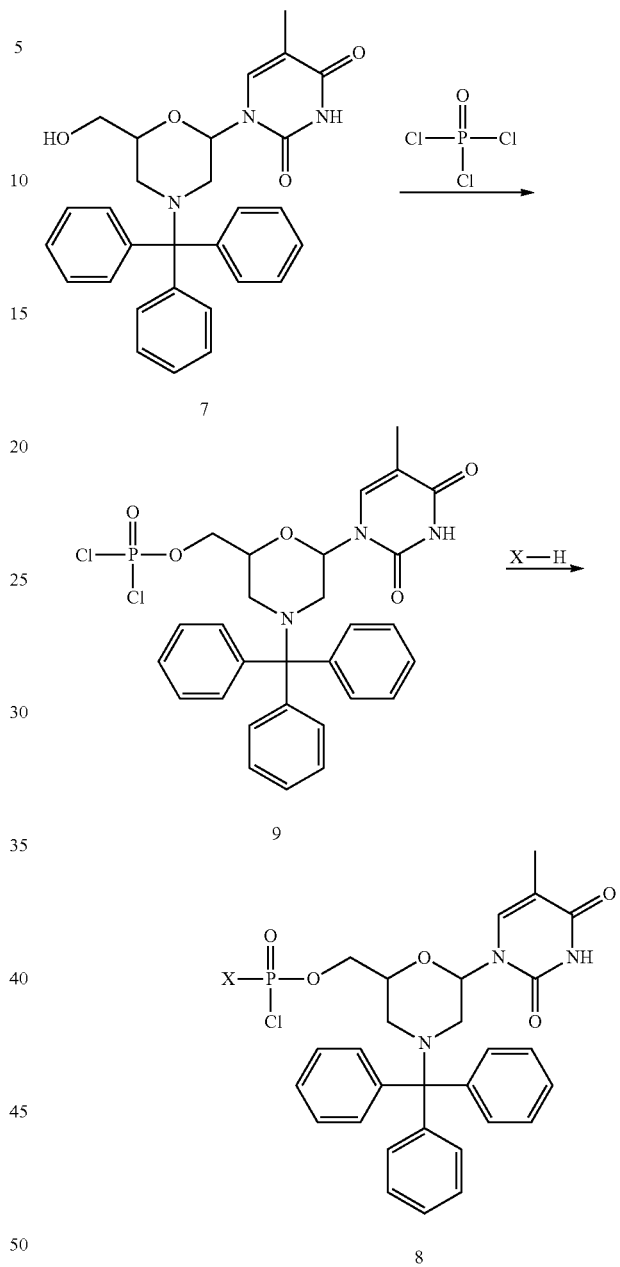

To a solution of $POCl_3$ (1.1 eq) in dichloromethane was added 2,6-lutidine (2 eq), followed by dropwise addition of Mo(Tr)T (7) (1 eq)/dichloromethane solution at 0° C. After 1 hour, the reaction solution was diluted with dichloromethane, and quickly washed three times with 10% aqueous citric acid. The desired phosphodichloridate (9) was obtained after drying over $MgSO_4$ and evaporation of solvent.

To a solution of the phosphodichloridate (1 eq) in dichloromethane was added amine (1 eq)/dichloromethane dropwise to the solution at 0° C. After 15 minutes, the reaction mixture was allowed to warm to room temperature for about an hour. Upon reaction completion, the product (8) as a white solid was collected by precipitation with the addition of hexanes, followed by filtration. The product was stored at −20° C. after drying under vacuum. The structure was confirmed by LCMS analysis.

Example 1: ((2S,6R)-6-(5-methyl-2,4-dioxo-3,4-dihydropyrimidin-1(2H)-yl)-4-tritylmorpholin-2-yl)methyl phosphorodichloridate

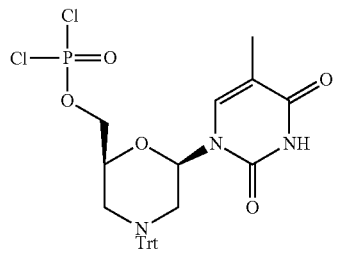

To a cooled (ice/water bath) DCM solution (20 mL) of phosphorus oxychloride (2.12 mL, 22.7 mmol) was added dropwise 2,6-lutidine (4.82 mL, 41.4 mmol) then a DCM solution (20 mL) Mo(Tr)T (2) (10.0 g, 20.7 mmol) was added dropwise over 15 min (int. temp. 0-10° C.) then bath was removed a stirring continued at ambient temperature for 20 min. The reaction was washed with citric acid solution (40 mL×3, 10% w/v aq), dried (MgSO$_4$), filtered and concentrated to a white foam (9.79 g) then used directly for the following procedure.

Example 2: (6-(5-methyl-2,4-dioxo-3,4-dihydropyrimidin-1(2H)-yl)-4-tritylmorpholin-2-yl)methyl (4-(dimethylamino)piperidin-1-yl)phosphonochloridate

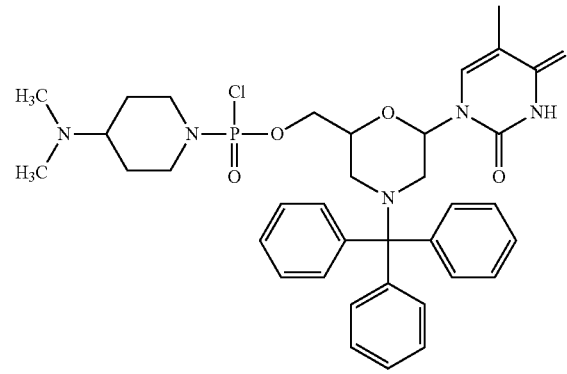

To a cooled (ice/water bath) DCM solution (5 mL) of the dichlorophosphate from example 1 (5.00 g, 5.00 mmol) was added a DCM solution (5 mL) of the piperidine (0.61 g, 4.76 mmol) dropwise then the bath was removed and stirring continued at ambient temperature for 30 min. The reaction was loaded directly onto a column. Chromatography with [SiO$_2$ column (40 g), DCM/EtOH eluant (gradient 1:0 to 1:1)] afforded the title compound (2.5 g) as a white foam.

ESI/MS calcd. for 1-(4-nitrophenyl)piperazine derivative C$_{46}$H$_{55}$N$_8$O$_7$P 862.4, found m/z=863.6 (M+1).

Example 3: 1-(1-(chloro((6-(5-methyl-2,4-dioxo-3,4-dihydropyrimidin-1(2H)-yl)-4-tritylmorpholin-2-yl)methoxy)phosphoryl)piperidin-4-yl)-1-methylpyrrolidin-1-ium chloride

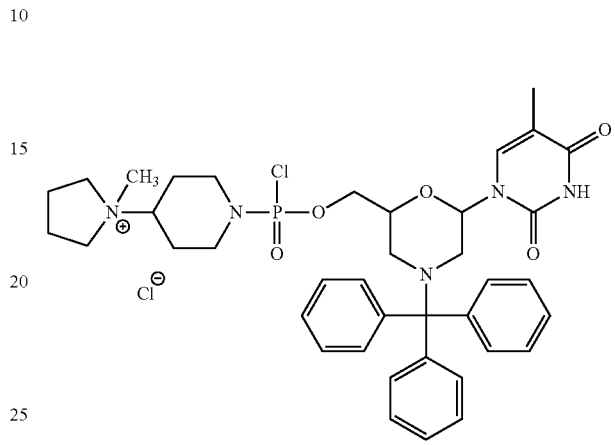

The title compound was synthesized in a manner analogous to that described in Example 2 to afford the title compound (0.6 g) as a white solid. ESI/MS calcd. for 1-(4-nitrophenyl)piperazine derivative C$_{49}$H$_{60}$N$_8$O$_7$P 903.4, found m/z=903.7 (M+).

Example 4: ((2S,6R)-6-(5-methyl-2,4-dioxo-3,4-dihydropyrimidin-1(2H)-yl)-4-tritylmorpholin-2-yl)methyl (4-methylpiperazin-1-yl)phosphonochloridate

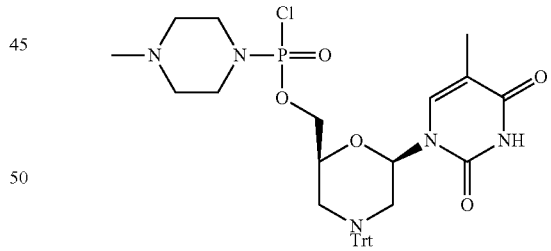

To a cooled (ice/water bath) DCM solution (10 mL) of phosphorus oxychloride (1.02 mL, 11.0 mmol) was added dropwise 2,6-lutidine (3.49 mL, 29.9 mmol) then a DCM solution (10 mL) of methyl piperazine (1.00 g, 10.0 mmol) was added dropwise and stirring continued for 1 h. A DCM solution (10 mL) of Mo(Tr)T (2) (4.82, 10.0 mmol) and NMI (79 µL, 1.0 mmol) was added and stirred 4 h then loaded directly onto a column. Chromatography with [SiO$_2$ column (80 g), DCM/Acetone with 2% TEA eluent (gradient 1:0 to 0:1)] afforded the title compound (0.8 g) as a white foam. ESI/MS calcd. for 1-(4-nitrophenyl)piperazine derivative C$_{43}$H$_{48}$N$_7$O$_8$P 834.4, found m/z=835.5 (M+1).

Example 5: ((2S,6R)-6-(5-methyl-2,4-dioxo-3,4-dihydropyrimidin-1(2H)-yl)-4-tritylmorpholin-2-yl)methyl (4-ethylpiperazin-1-yl)phosphonochloridate

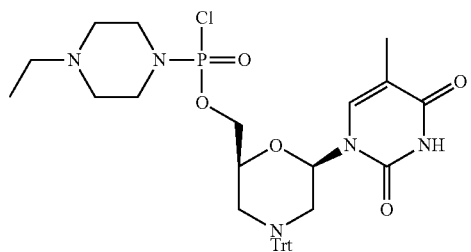

The title compound was synthesized in a manner analogous to that described in Example 4 to afford the title compound (11.5 g) as a white foam. ESI/MS calcd. for 1-(4-nitrophenyl)piperazine derivative $C_{45}H_{53}N_8O_7P$ 848.4, found m/z=849.7 (M+1).

Example 6: ((2S,6R)-6-(6-benzamido-9H-purin-9-yl)-4-tritylmorpholin-2-yl)methyl (4-ethylpiperazin-1-yl)phosphonochloridate

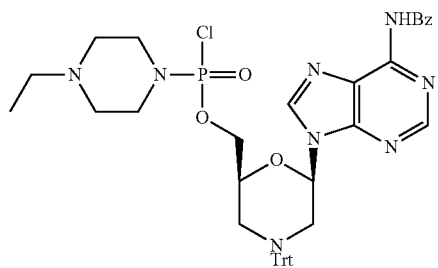

The title compound was synthesized in a manner analogous to that described in Example 4 to afford the title compound (4.5 g) as a white foam. ESI/MS calcd. for 1-(4-nitrophenyl)piperazine derivative $C_{52}H_{56}N_{11}O_6P$ 961.4, found m/z=962.8 (M+1).

Example 7: ((2S,6R)-6-(5-methyl-2,4-dioxo-3,4-dihydropyrimidin-1(2H)-yl)-4-tritylmorpholin-2-yl)methyl (4-isopropylpiperazin-1-yl)phosphonochloridate

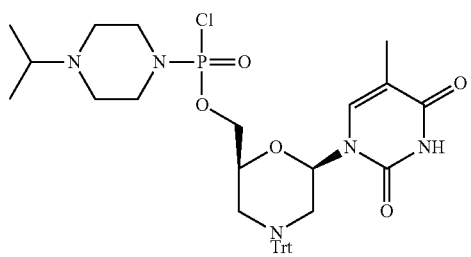

The title compound was synthesized in a manner analogous to that described in Example 4 to afford the title compound (3.5 g) as a white foam. ESI/MS calcd. for 1-(4-nitrophenyl)piperazine derivative $C_{46}H_{55}N_8O_7P$ 862.4, found m/z=863.7 (M+1).

Example 8: ((2S,6R)-6-(5-methyl-2,4-dioxo-3,4-dihydropyrimidin-1(2H)-yl)-4-tritylmorpholin-2-yl)methyl methyl(2-(2,2,2-trifluoroacetamido)ethyl)phosphoramidochloridate

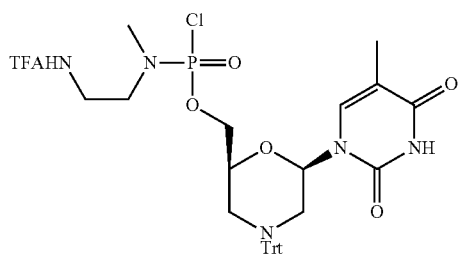

The title compound was synthesized in a manner analogous to that described in Example 4 to afford the title compound (1.0 g) as a white foam. ESI/MS calcd. for 1-(4-nitrophenyl)piperazine derivative $C_{44}H_{48}F_3N_8O_8P$ 904.3, found m/z=903.7 (M−1).

Example 9: ((2S,6R)-6-(5-methyl-2,4-dioxo-3,4-dihydropyrimidin-1(2H)-yl)-4-tritylmorpholin-2-yl)methyl methyl(2-(2,2,2-trifluoro-N-methylacetamido)ethyl)phosphoramidochloridate

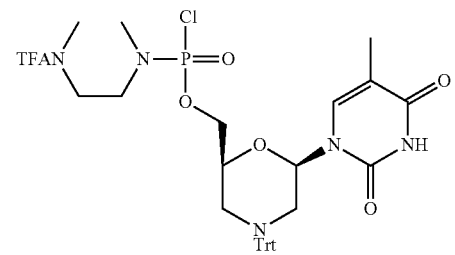

The title compound was synthesized in a manner analogous to that described in Example 4 to afford the title compound (1.8 g) as a white foam. ESI/MS calcd. for 1-(4-nitrophenyl)piperazine derivative $C_{45}H_{50}F_3N_8O_8P$ 918.3, found m/z=1836.6 (2M+).

Example 10: ((2S,6R)-6-(5-methyl-2,4-dioxo-3,4-dihydropyrimidin-1(2H)-yl)-4-tritylmorpholin-2-yl)methyl (4-(2,2,2-trifluoroacetamido)piperidin-1-yl)phosphonochloridate

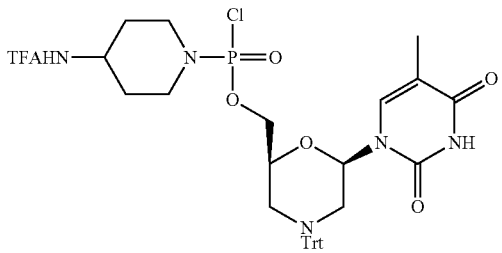

To a cooled solution (ice/water bath) of phosphorus oxychloride (17.7 mL, 190 mmol) in DCM (190 mL) was added dropwise 2,6-lutidine (101 mL, 864 mmol) then Mo(Tr)T (2) (83.5 g, 173 mmol) portionwise over 15 min (int. temp. 0-10° C.) and stirred. After 30 min, the 4-aminopiperidine monotrifluoroacetamide (48.9 g, ~190 mmol) was added dropwise over 15 min (int. temp. 0-8° C.) and stirred. After 1 h, DIPEA (50 mL) was added dropwise (int. temp. 0-10° C.) and stirred 1 h. The reaction was washed with citric acid solution (500 mL×3, 10% w/v aq), dried (MgSO$_4$), filtered and concentrated to a viscous oil which was loaded directly onto a column. Chromatography with [SiO$_2$ column (330 g), hexanes/EtOAc eluant (gradient 1:0 to 0:1)] afforded the title compound (91.3 g, 70% yield) as a white foam. ESI/MS calcd. for 1-(4-nitrophenyl)piperazine derivative C$_{43}$H$_{48}$N$_7$O$_8$P 930.9, found m/z=954.4 (M+Na).

Examples 13-37 were prepared via procedure A described above.

Example 11: (6-(5-methyl-2,4-dioxo-3,4-dihydropyrimidin-1(2H)-yl)-4-tritylmorpholin-2-yl)methyl (4-(1-(2,2,2-trifluoroacetyl)piperidin-4-yl)piperazin-1-yl)phosphonochloridate

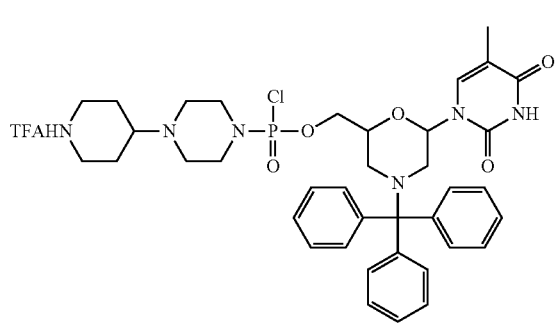

Example 12: (6-(5-methyl-2,4-dioxo-3,4-dihydropyrimidin-1(2H)-yl)-4-tritylmorpholin-2-yl)methyl (4-morpholinopiperidin-1-yl)phosphonochloridate

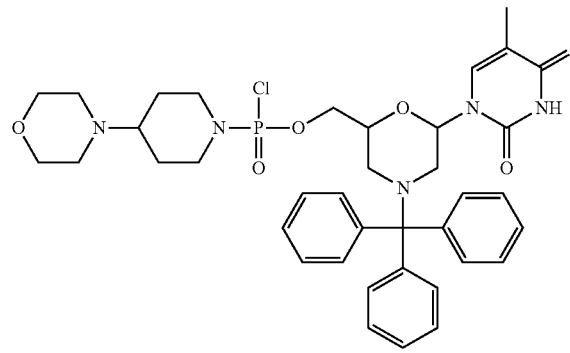

Example 13: (6-(5-methyl-2,4-dioxo-3,4-dihydropyrimidin-1(2H)-yl)-4-tritylmorpholin-2-yl)methyl bis(3-(2,2,2-trifluoroacetamido)propyl)phosphoramidochloridate

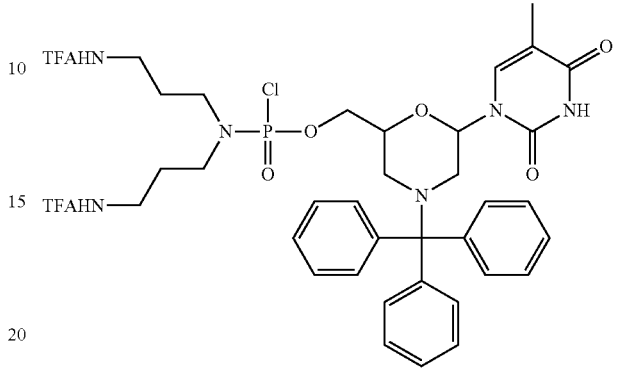

Example 14: (6-(5-methyl-2,4-dioxo-3,4-dihydropyrimidin-1(2H)-yl)-4-tritylmorpholin-2-yl)methyl [1,4'-bipiperidin]-1'-ylphosphonochloridate

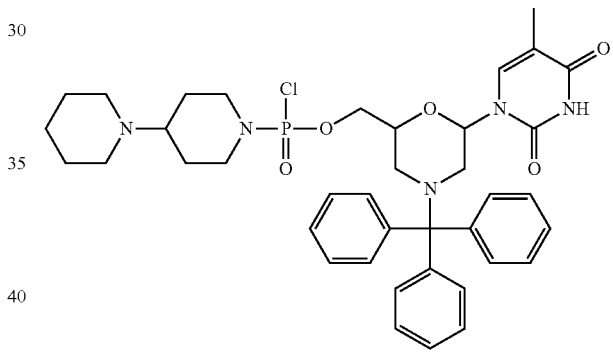

Examples 15 through 20 below were prepared via procedure B described above.

Example 15: (6-(5-methyl-2,4-dioxo-3,4-dihydropyrimidin-1(2H)-yl)-4-tritylmorpholin-2-yl)methyl (4-(pyrimidin-2-yl)piperazin-1-yl)phosphonochloridate

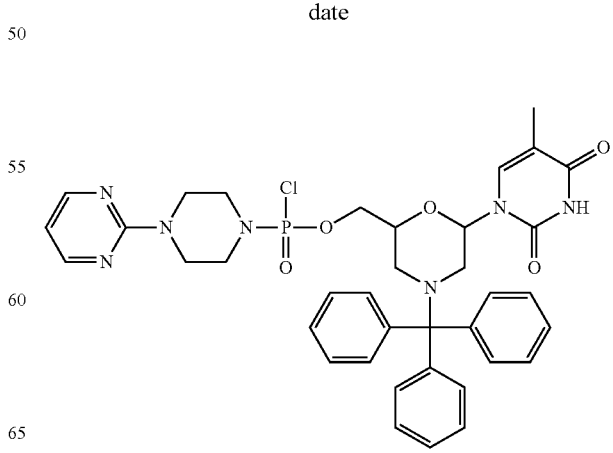

Example 16: (6-(5-methyl-2,4-dioxo-3,4-dihydropyrimidin-1(2H)-yl)-4-tritylmorpholin-2-yl)methyl (4-(2-(dimethylamino)ethyl)piperazin-1-yl)phosphonochloridate

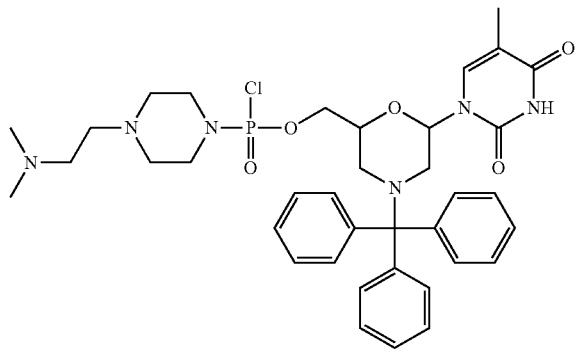 [SMILES: Cc1cn(C2CN(C(c3ccccc3)(c3ccccc3)c3ccccc3)CC(COP(=O)(Cl)N3CCN(CCN(C)C)CC3)O2)c(=O)[nH]c1=O]

Example 17: (6-(5-methyl-2,4-dioxo-3,4-dihydropyrimidin-1(2H)-yl)-4-tritylmorpholin-2-yl)methyl (4-phenylpiperazin-1-yl)phosphonochloridate

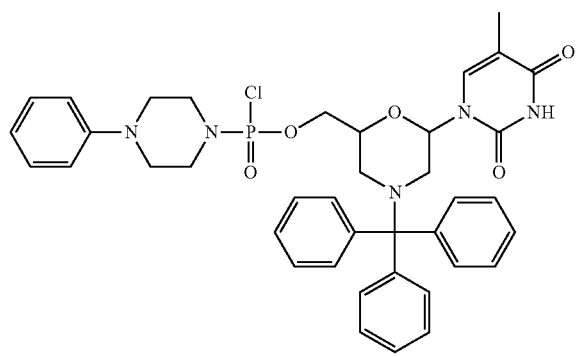 [SMILES: Cc1cn(C2CN(C(c3ccccc3)(c3ccccc3)c3ccccc3)CC(COP(=O)(Cl)N3CCN(c4ccccc4)CC3)O2)c(=O)[nH]c1=O]

Example 18: (6-(5-methyl-2,4-dioxo-3,4-dihydropyrimidin-1(2H)-yl)-4-tritylmorpholin-2-yl)methyl (4-(2,2,2-trifluoro-N-methylacetamido)piperidin-1-yl)phosphonochloridate

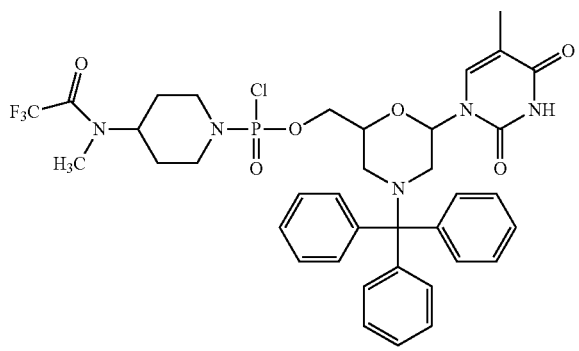 [SMILES: Cc1cn(C2CN(C(c3ccccc3)(c3ccccc3)c3ccccc3)CC(COP(=O)(Cl)N3CCC(N(C)C(=O)C(F)(F)F)CC3)O2)c(=O)[nH]c1=O]

Example 19: (6-(5-methyl-2,4-dioxo-3,4-dihydropyrimidin-1(2H)-yl)-4-tritylmorpholin-2-yl)methyl methyl(3-(2,2,2-trifluoro-N-methylacetamido)propyl)phosphoramidochloridate

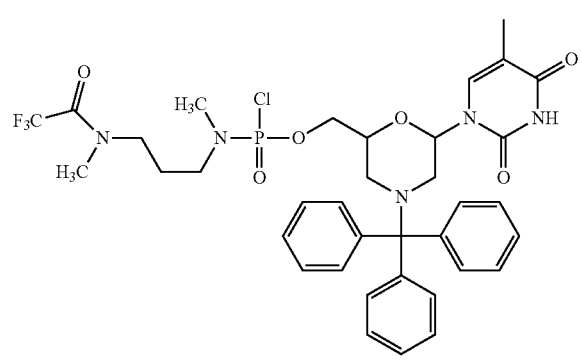 [SMILES: Cc1cn(C2CN(C(c3ccccc3)(c3ccccc3)c3ccccc3)CC(COP(=O)(Cl)N(C)CCCN(C)C(=O)C(F)(F)F)O2)c(=O)[nH]c1=O]

Example 20: ((2S,6R)-6-(6-benzamido-9H-purin-9-yl)-4-tritylmorpholin-2-yl)methyl (4-(2,2,2-trifluoroacetamido)piperidin-1-yl)phosphonochloridate

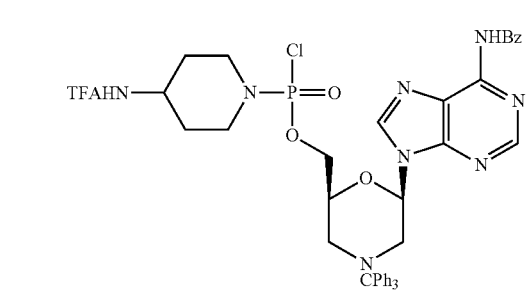

Example 21: (4-(pyrrolidin-1-yl)piperidin-1-yl)phosphonic dichloride hydrochloride

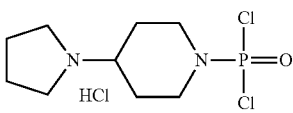 [SMILES: O=P(Cl)(Cl)N1CCC(N2CCCC2)CC1 ; Cl]

To a cooled (ice/water bath) solution of phosphorus oxychloride (5.70 mL, 55.6 mmol) in DCM (30 mL) was added 2,6-lutidine (19.4 mL, 167 mmol) and a DCM solution (30 mL) of 4-(1-pyrrolidinyl)-piperidine (8.58 g, 55.6 mmol) and stirred for 1 hour. The suspension was filtered and solid washed with excess diethyl ether to afford the title pyrrolidine (17.7 g, 91% yield) as a white solid. ESI/MS calcd. for 1-(4-nitrophenyl)piperazine derivative $C_{19}H_{30}N_5O_4P$ 423.2, found m/z=422.2 (M−1).

Example 22: ((2S,6R)-6-(5-methyl-2,4-dioxo-3,4-dihydropyrimidin-1(2H)-yl)-4-tritylmorpholin-2-yl)methyl (4-(pyrrolidin-1-yl)piperidin-1-yl)phosphonochloridate hydrochloride

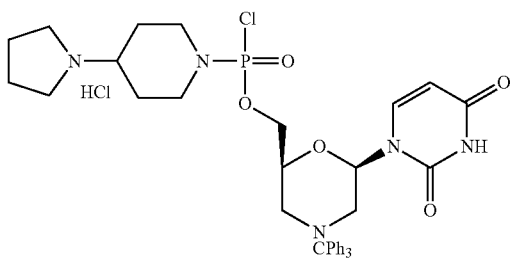

To a stirred, cooled (ice/water bath) solution of the dichlorophosphoramidate from Example 21 (17.7 g, 50.6 mmol) in DCM (100 mL) was added a DCM solution (100 mL) of Mo(Tr)T (2) (24.5 g, 50.6 mmol), 2,6-Lutidine (17.7 mL, 152 mmol), and 1-methylimidazole (0.401 mL, 5.06 mmol) dropwise over 10 minutes. The bath was allowed to warm to ambient temperature as suspension was stirred. After 6 hours, the suspension was poured onto diethyl ether (1 L), stirred 15 minutes, filtered and solid washed with additional ether to afford a white solid (45.4 g). The crude product was purified by chromatography [SiO$_2$ column (120 gram), DCM/MeOH eluant (gradient 1:0 to 6:4)], and the combined fractions were poured onto diethyl ether (2.5 L), stirred 15 min, filtered, and the resulting solid washed with additional ether to afford the title compound (23.1 g, 60% yield) as a white solid. ESI/MS calcd. for 1-(4-nitrophenyl) piperazine derivative C$_{48}$H$_{57}$N$_8$O$_7$P 888.4, found m/z=887.6 (M−1).

Example 23: Preparation of Morpholino Oligomers

Preparation of trityl piperazine phenyl carbamate 1b (see FIG. 1): To a cooled suspension of compound 1a in dichloromethane (6 mL/g 11) was added a solution of potassium carbonate (3.2 eq) in water (4 mL/g potassium carbonate). To this two-phase mixture was slowly added a solution of phenyl chloroformate (1.03 eq) in dichloromethane (2 g/g phenyl chloroformate). The reaction mixture was warmed to 20° C. Upon reaction completion (1-2 hr), the layers were separated. The organic layer was washed with water, and dried over anhydrous potassium carbonate. The product 1b was isolated by crystallization from acetonitrile. Yield=80%.

Preparation of carbamate alcohol 1c: Sodium hydride (1.2 eq) was suspended in 1-methyl-2-pyrrolidinone (32 mL/g sodium hydride). To this suspension were added triethylene glycol (10.0 eq) and compound 1b (1.0 eq). The resulting slurry was heated to 95° C. Upon reaction completion (1-2 hr), the mixture was cooled to 20° C. To this mixture was added 30% dichloromethane/methyl tert-butyl ether (v:v) and water. The product-containing organic layer was washed successively with aqueous NaOH, aqueous succinic acid, and saturated aqueous sodium chloride. The product 1c was isolated by crystallization from dichloromethane/methyl tert-butyl ether/heptane. Yield=90%.

Preparation of Tail acid 1d: To a solution of compound 1c in tetrahydrofuran (7 mL/g 36) was added succinic anhydride (2.0 eq) and DMAP (0.5 eq). The mixture was heated to 50° C. Upon reaction completion (5 hr), the mixture was cooled to 20° C. and adjusted to pH 8.5 with aqueous NaHCO3. Methyl tert-butyl ether was added, and the product was extracted into the aqueous layer. Dichloromethane was added, and the mixture was adjusted to pH 3 with aqueous citric acid. The product-containing organic layer was washed with a mixture of pH=3 citrate buffer and saturated aqueous sodium chloride. This dichloromethane solution of 1d was used without isolation in the preparation of compound 1e.

Preparation of 1e: To the solution of compound 1d was added N-hydroxy-5-norbornene-2,3-dicarboxylic acid imide (HONB) (1.02 eq), 4-dimethylaminopyridine (DMAP) (0.34 eq), and then 1-(3-dimethylaminopropyl)-N'-ethylcarbodiimide hydrochloride (EDC) (1.1 eq). The mixture was heated to 55° C. Upon reaction completion (4-5 hr), the mixture was cooled to 20° C. and washed successively with 1:1 0.2 M citric acid/brine and brine. The dichloromethane solution underwent solvent exchange to acetone and then to N,N-dimethylformamide, and the product was isolated by precipitation from acetone/N,N-dimethylformamide into saturated aqueous sodium chloride. The crude product was reslurried several times in water to remove residual N,N-dimethylformamide and salts. Yield=70% of 1e from compound 1c. Introduction of the activated "Tail" onto the disulfide anchor-resin was performed in NMP by the procedure used for incorporation of the subunits during solid phase synthesis.

Preparation of the Solid Support for Synthesis of Morpholino Oligomers (see FIG. 2): This procedure was performed in a silanized, jacketed peptide vessel (custom made by ChemGlass, NJ, USA) with a coarse porosity (40-60 μm) glass frit, overhead stirrer, and 3-way Teflon stopcock to allow N2 to bubble up through the frit or a vacuum extraction. Temperature control was achieved in the reaction vessel by a circulating water bath.

The resin treatment/wash steps in the following procedure consist of two basic operations: resin fluidization and solvent/solution extraction. For resin fluidization, the stopcock was positioned to allow N2 flow up through the frit and the specified resin treatment/wash was added to the reactor and allowed to permeate and completely wet the resin. Mixing was then started and the resin slurry mixed for the specified time. For solvent/solution extraction, mixing and N2 flow were stopped and the vacuum pump was started and then the stopcock was positioned to allow evacuation of resin treatment/wash to waste. All resin treatment/wash volumes were 15 mL/g of resin unless noted otherwise.

To aminomethylpolystyrene resin (100-200 mesh; ~1.0 mmol/g N2 substitution; 75 g, 1 eq, Polymer Labs, UK, part #1464-X799) in a silanized, jacketed peptide vessel was added 1-methyl-2-pyrrolidinone (NMP; 20 ml/g resin) and the resin was allowed to swell with mixing for 1-2 hr. Following evacuation of the swell solvent, the resin was washed with dichloromethane (2×1-2 min), 5% diisopropylethylamine in 25% isopropanol/dichloromethane (2×3-4 min) and dichloromethane (2×1-2 min). After evacuation of the final wash, the resin was fluidized with a solution of disulfide anchor 2a in 1-methyl-2-pyrrolidinone (0.17 M; 15 mL/g resin, ~2.5 eq) and the resin/reagent mixture was heated at 45° C. for 60 hr. On reaction completion, heating was discontinued and the anchor solution was evacuated and the resin washed with 1-methyl-2-pyrrolidinone (4×3-4 min) and dichloromethane (6×1-2 min). The resin was treated with a solution of 10% (v/v) diethyl dicarbonate in dichloromethane (16 mL/g; 2×5-6 min) and then washed with dichloromethane (6×1-2 min). The resin 2b was dried under a N2 stream for 1-3 hr and then under vacuum to constant weight (±2%). Yield: 110-150% of the original resin weight.

Determination of the Loading of Aminomethylpolystyrene-disulfide resin: The loading of the resin (number of potentially available reactive sites) is determined by a spectrometric assay for the number of triphenylmethyl (trityl) groups per gram of resin.

A known weight of dried resin (25±3 mg) is transferred to a silanized 25 ml volumetric flask and ~5 mL of 2% (v/v) trifluoroacetic acid in dichloromethane is added. The contents are mixed by gentle swirling and then allowed to stand for 30 min. The volume is brought up to 25 mL with additional 2% (v/v) trifluoroacetic acid in dichloromethane and the contents thoroughly mixed. Using a positive displacement pipette, an aliquot of the trityl-containing solution (500 µL) is transferred to a 10 mL volumetric flask and the volume brought up to 10 mL with methanesulfonic acid.

The trityl cation content in the final solution is measured by UV absorbance at 431.7 nm and the resin loading calculated in trityl groups per gram resin (µmol/g) using the appropriate volumes, dilutions, extinction coefficient (ε: 41 µmol-1 cm$^{-1}$) and resin weight. The assay is performed in triplicate and an average loading calculated.

The resin loading procedure in this example will provide resin with a loading of approximately 500 µmol/g. A loading of 300-400 in µmol/g was obtained if the disulfide anchor incorporation step is performed for 24 hr at room temperature.

Tail loading: Using the same setup and volumes as for the preparation of aminomethylpolystyrene-disulfide resin, the Tail can be introduced into the molecule. For the coupling step, a solution of 1e (0.2 M) in NMP containing 4-ethylmorpholine (NEM, 0.4 M) was used instead of the disulfide anchor solution. After 2 hr at 45° C., the resin 2b was washed twice with 5% diisopropylethylamine in 25% isopropanol/dichloromethane and once with DCM. To the resin was added a solution of benzoic anhydride (0.4 M) and NEM (0.4 M). After 25 min, the reactor jacket was cooled to room temperature, and the resin washed twice with 5% diisopropylethylamine in 25% isopropanol/dichloromethane and eight times with DCM. The resin 2c was filtered and dried under high vacuum. The loading for resin 2c is defined to be the loading of the original aminomethylpolystyrene-disulfide resin 2b used in the Tail loading.

Solid Phase Synthesis: Morpholino Oligomers were prepared on a Gilson AMS-422 Automated Peptide Synthesizer in 2 mL Gilson polypropylene reaction columns (Part #3980270). An aluminum block with channels for water flow was placed around the columns as they sat on the synthesizer. The AMS-422 will alternatively add reagent/wash solutions, hold for a specified time, and evacuate the columns using vacuum.

For oligomers in the range up to about 25 subunits in length, aminomethylpolystyrene-disulfide resin with loading near 500 µmol/g of resin is preferred. For larger oligomers, aminomethylpolystyrene-disulfide resin with loading of 300-400 µmol/g of resin is preferred. If a molecule with 5'-Tail is desired, resin that has been loaded with Tail is chosen with the same loading guidelines.

The following reagent solutions were prepared:

Detrylation Solution: 10% Cyanoacetic Acid (w/v) in 4:1 dichloromethane/acetonitrile; Neutralization Solution: 5% Diisopropylethylamine in 3:1 dichloromethane/isopropanol; Coupling Solution: 0.18 M (or 0.24 M for oligomers having grown longer than 20 subunits) activated Morpholino Subunit of the desired base and linkage type and 0.4 M N ethylmorpholine, in 1,3-dimethylimidazolidinone. Dichloromethane (DCM) was used as a transitional wash separating the different reagent solution washes.

On the synthesizer, with the block set to 42° C., to each column containing 30 mg of aminomethylpolystyrene-disulfide resin (or Tail resin) was added 2 mL of 1-methyl-2-pyrrolidinone and allowed to sit at room temperature for 30 min. After washing with 2 times 2 mL of dichloromethane, the following synthesis cycle was employed:

| Step | Volume | Delivery | Hold time |
| --- | --- | --- | --- |
| Detrylation | 1.5 mL | Manifold | 15 seconds |
| Detrylation | 1.5 mL | Manifold | 15 seconds |
| Detrylation | 1.5 mL | Manifold | 15 seconds |
| Detrylation | 1.5 mL | Manifold | 15 seconds |
| Detrylation | 1.5 mL | Manifold | 15 seconds |
| Detrylation | 1.5 mL | Manifold | 15 seconds |
| Detrylation | 1.5 mL | Manifold | 15 seconds |
| DCM | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| Coupling | 350 uL-500 uL | Syringe | 40 minutes |
| DCM | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| DCM | 1.5 mL | Manifold | 30 seconds |
| DCM | 1.5 mL | Manifold | 30 seconds |

The sequences of the individual oligomers were programmed into the synthesizer so that each column receives the proper coupling solution (A, C, G, T, I) in the proper sequence. When the oligomer in a column had completed incorporation of its final subunit, the column was removed from the block and a final cycle performed manually with a coupling solution comprised of 4-methoxytriphenylmethyl chloride (0.32 M in DMI) containing 0.89 M 4-ethylmorpholine.

Cleavage from the resin and removal of bases and backbone protecting groups: After methoxytritylation, the resin was washed 8 times with 2 mL 1-methyl-2-pyrrolidinone. One mL of a cleavage solution consisting of 0.1 M 1,4-dithiothreitol (DTT) and 0.73 M triethylamine in 1-methyl-2-pyrrolidinone was added, the column capped, and allowed to sit at room temperature for 30 min. After that time, the solution was drained into a 12 mL Wheaton vial. The greatly shrunken resin was washed twice with 300 µL of cleavage solution. To the solution was added 4.0 mL conc aqueous ammonia (stored at −20° C.), the vial capped tightly (with Teflon lined screw cap), and the mixture swirled to mix the solution. The vial was placed in a 45° C. oven for 16-24 hr to effect cleavage of base and backbone protecting groups.

Initial Oligomer Isolation: The vialed ammonolysis solution was removed from the oven and allowed to cool to room temperature. The solution was diluted with 20 mL of 0.28% aqueous ammonia and passed through a 2.5×10 cm column containing Macroprep HQ resin (BioRad). A salt gradient (A: 0.28% ammonia with B: 1 M sodium chloride in 0.28% ammonia; 0-100% B in 60 min) was used to elute the methoxytrityl containing peak. The combined fractions were pooled and further processed depending on the desired product.

Demethoxytritylation of Morpholino Oligomers: The pooled fractions from the Macroprep purification were treated with 1 M H3PO4 to lower the pH to 2.5. After initial mixing, the samples sat at room temperature for 4 min, at which time they are neutralized to pH 10-11 with 2.8% ammonia/water. The products were purified by solid phase extraction (SPE).

Amberchrome CG-300M (Rohm and Haas; Philadelphia, Pa.) (3 mL) is packed into 20 mL fritted columns (BioRad Econo-Pac Chromatography Columns (732-1011)) and the resin rinsed with 3 mL of the following: 0.28% NH4OH/ 80% acetonitrile; 0.5M NaOH/20% ethanol; water; 50 mM H3PO4/80% acetonitrile; water; 0.5 NaOH/20% ethanol; water; 0.28% NH4OH.

The solution from the demethoxytritylation was loaded onto the column and the resin rinsed three times with 3-6 mL 0.28% aqueous ammonia. A Wheaton vial (12 mL) was placed under the column and the product eluted by two washes with 2 mL of 45% acetonitrile in 0.28% aqueous ammonia. The solutions were frozen in dry ice and the vials placed in a freeze dryer to produce a fluffy white powder. The samples were dissolved in water, filtered through a 0.22 micron filter (Pall Life Sciences, Acrodisc 25 mm syringe filter, with a 0.2 micron HT Tuffryn membrane) using a syringe and the Optical Density (OD) was measured on a UV spectrophotometer to determine the OD units of oligomer present, as well as dispense sample for analysis. The solutions were then placed back in Wheaton vials for lyophilization.

Analysis of Morpholino Oligomers: MALDI-TOF mass spectrometry was used to determine the composition of fractions in purifications as well as provide evidence for identity (molecular weight) of the oligomers. Samples were run following dilution with solution of 3,5-dimethoxy-4-hydroxycinnamic acid (sinapinic acid), 3,4,5-trihydroxyacetophenone (THAP) or alpha-cyano-4-hydroxycinnamic acid (HCCA) as matrices.

Cation exchange (SCX) HPLC was performed using a Dionex ProPac SCX-10, 4×250 mm column (Dionex Corporation; Sunnyvale, Calif.) using 25 mM pH=5 sodium acetate 25% acetonitrile (Buffer A) and 25 mM pH=5 sodium acetate 25% acetonitrile 1.5 M potassium chloride (buffer B) (Gradient 10-100% B in 15 min) or 25 mM KH2PO4 25% acetonitrile at pH=3.5 (buffer A) and 25 mM KH2PO4 25% acetonitrile at pH=3.5 with 1.5 M potassium chloride (buffer B) (Gradient 0-35% B in 15 min). The former system was used for positively charged oligomers that do not have a peptide attached, while the latter was used for peptide conjugates.

Purification of Morpholino Oligomers by Cation Exchange Chromatography: The sample is dissolved in 20 mM sodium acetate, pH=4.5 (buffer A) and applied to a column of Source 30 cation exchange resin (GE Healthcare) and eluted with a gradient of 0.5 M sodium chloride in 20 mM sodium acetate and 40% acetonitrile, pH=4.5 (buffer B). The pooled fractions containing product are neutralized with conc aqueous ammonia and applied to an Amberchrome SPE column. The product is eluted, frozen, and lyophilized as above.

Example 24: APN Oligonucleotide Modification Enhances SMN2 Exon 7 Inclusion

Figure 7:
FIG. 7: RT-PCR of SMN2. RNA from GM03813 fibroblasts nucleofected with the E8/4b APN-modified oligonucleotide at the indicated concentrations were RT-PCR amplified as described in the Methods. Gels containing the resulting reactions were analyzed as described in the Methods and in FIG. 6.
Figure 8:
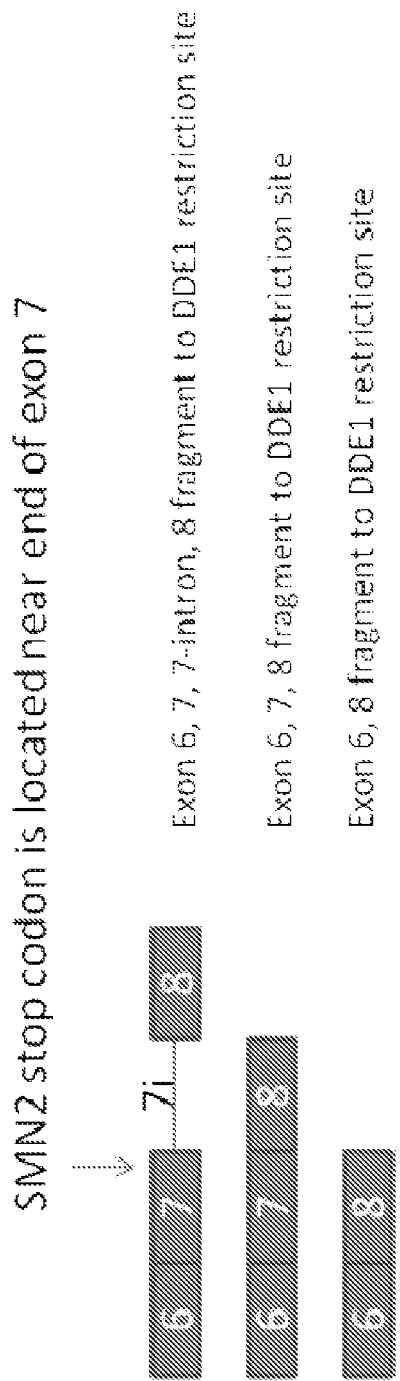
FIG. 8: As is shown in FIG. 7 the invention provides for a method for enhancing the level of exon 7-containing SMN2 mRNA relative to exon-deleted SMN2 mRNA in a cell. This is shown schematically in this figure. The largest band on the gel in FIG. 7. corresponds to a cDNA containing Exons 6, 7, intron-7 and Exon 8. The middle band contains a reverse transcription product containing Exons 6, 7, and Exon 8. The lowest band corresponds to Exons 6 and 8. Thus, the treatment of cells with the APN oligonucleotide increase the higher molecular weight bands corresponding to the inclusion of Exon 7 in the cDNA. Since Exon 7 includes a stop codon the protein product of both high molecular weight cDNAs will be the same.
Figure 9:
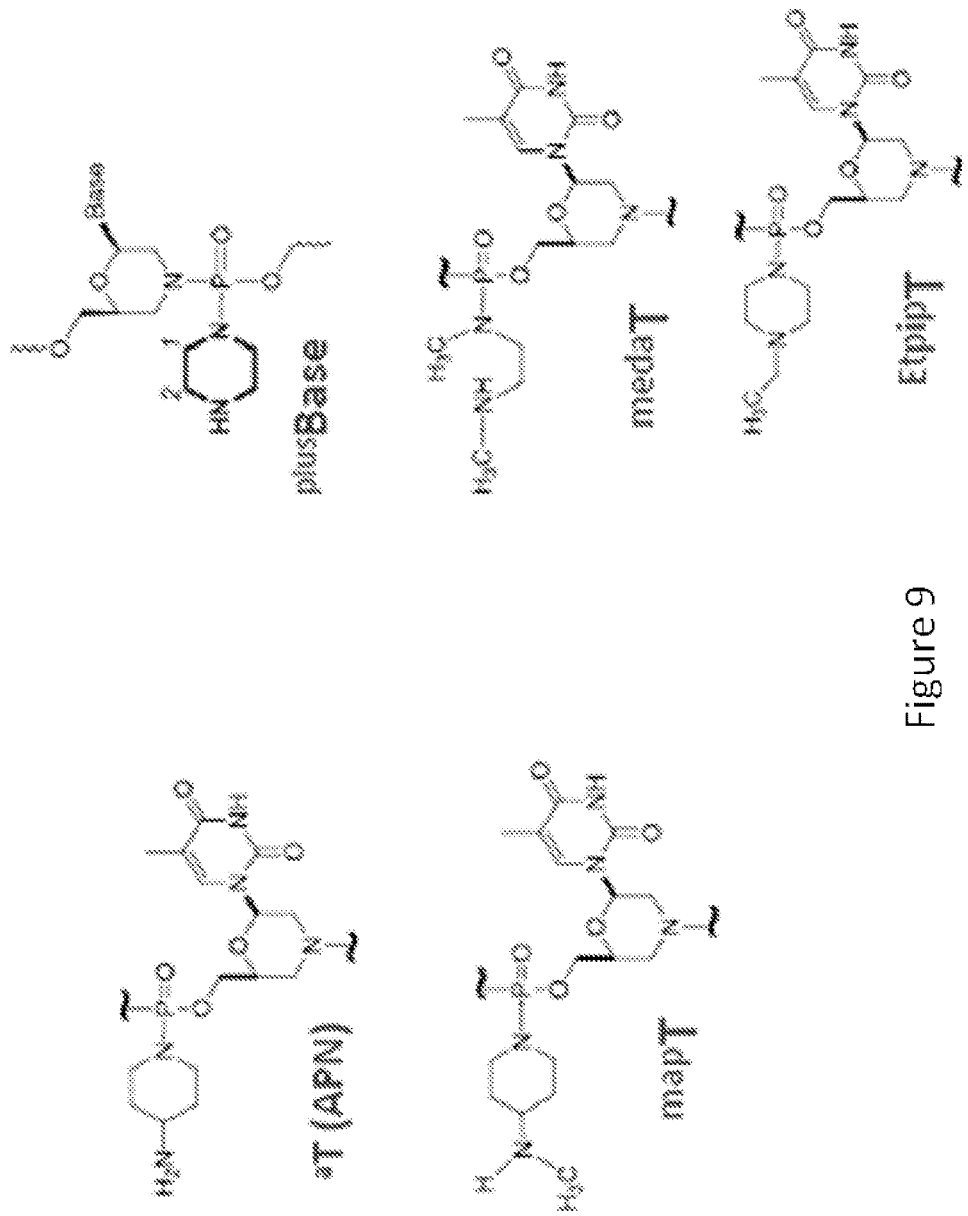
FIG. 9: Exemplary structures of APN- and plus-related cationic modifications. Shown are exemplary species of APN-related and plus-related cationic modifications. APN-related modifications include APN and mapT, and plus-related modifications include plusT, medaT, and etpipT. Although the exemplified modifications relate to thymine, any base (e.g., thymine, cytosine, guanine, adenine) can be modified with the APN-related and plus-related cationic modifications.

Oligonucleotides containing the sequences shown in FIG. 5 were tested to determine whether the APN oligonucleotide would enhance SMN2 Exon 7 inclusion. Each of the oligonucleotides shown in Table 1 were introduced into cells using the Nucleofection Protocol described below. The results were quantified using the reverse transcriptase protocol and are shown in FIGS. 6 and 7. Intensity of the gel bands representing inclusion or exclusion of SMN2 exon 7 in GM03813 fibroblast cells (Coriell) were quantified with ImageQuant (GE). Exon 7 inclusion is reported as a percentage calculated from the ratio of the exon 7-included band intensities divided by the sum of the intensities from the exon 7-included and -excluded bands. Each dot represents the mean+/−1 standard deviation of two replicates at each concentration. Three independent experiments were combined to yield the above dataset. Percent inclusion analysis was performed in Microsoft Excel. Data points and curves were plotted in Graphpad Prism. As shown in FIG. 6 the addition of apn modifications to an oligonucleotide enhances the potency of the compound compared to unmodified PMO containing the same sequence. Thus, as shown in FIG. 6, 14 mer (11/15) APN was about an order of magnitude more potent than 14 mer (11/15) without the APN linkage. Likewise E8/4a-APN (11/15) and E8/4b-APN (11/15) were more potent than E8/4a (11/15) and E8/4b (11/15) respectively.

Example 25: SMA Cells Nucleofection Protocol

Patient-derived fibroblasts from an individual with Spinal Muscular Atrophy (Coriell cell line GM03813) were cultured according to standard protocols in Eagle's MEM with 10% FBS. Cells were passaged 3-5 days before the experiment and were approximately 80% confluent at nucleofection. Oligos were prepared as 1-2 mM stock solutions in nuclease-free water (not treated with DEPC) from which appropriate dilutions were made for nucleofection. Fibroblasts were trypsinized, counted, centrifuged at 90 g for 10 minutes, and 1-5×10e5 cells per well were resuspended in nucleofection Solution P2 (Lonza). Oligo solution and cells were then added to each well of a Nucleocuvette 16-well strip, and pulsed with program EN-100. Cells were incubated at room temperature for 10 minutes and transferred to a 12-well plate in duplicate. Total RNA was isolated from treated cells after 48 hours using the GE Illustra 96 Spin kit following the manufacturer's recommended protocol. Recovered RNA was stored at −80° C. prior to analysis.

Reverse transcriptase PCR was performed to amplify the SMN2 allele using the SuperScript III One-Step RT-PCR system (Invitrogen). 400 ng total RNA isolated from nucleofected cells was reverse transcribed and amplified with the following gene-specific primers and conditions (described in Hua 2007): E6-F: 5' ATA ATT CCC CCA CCA CCT CCC 3' (SEQ ID NO: 80); E8-467-R: 5' TTG CCA CAT ACG CCT CAC ATA C 3' (SEQ ID NO: 81); PCR Program: 60° C. for 30 min RT incubation; 94° C. denature, 55° C. anneal, 72° C. extension, 22 cycles. The amplification solution provided in the One-Step kit was supplemented with Cy5-labeled dCTP (GE) to enable band visualization by fluorescence. Following amplification, PCR products were digested with DDEI to differentiate between SMN1 or SMN2 alleles (as described in Hua 2007). Digested samples were run on a pre-cast 10% acrylamide/TBE gel (Invitrogen) and visualized on a Typhoon Trio (GE) using the 633 nm excitation laser and 670 nm BP 30 emission filter with the focal plane at the platen surface. Gels were analyzed with ImageQuant (GE) to determine the intensities of the bands. Intensities from all bands containing exon 7 were added together to represent the full exon 7 transcript levels in the inclusion analysis.

Example 26: SMA Mouse Model

SMNΔ7 mice can be used as an SMA model to characterize disease modifying antisense oligonucleotides. Mice possess only one Smn gene and the loss of this gene is embryonic lethal. To generate mice with an SMN deficiency that models human SMA, the human SMN2 gene can be introduced into mice. For example, two copies of human SMN2 can be introduced into mice lacking Smn to generate mice with severe SMA that may live an average of 5 days, while eight copies of SMN2 can be introduced to rescue the mice. In addition, SMN17, a SMN transgene lacking exon 7, can be introduced into the severe SMA mice to increase the average life span. Furthermore, SMN can be induced postnatally to modulate SMA in SMNΔ7 mice. Thus, the SMNΔ7 mouse can be used as an SMA model to characterize disease modifying antisense oligonucleotides.

Using the SMNΔ7 mouse model of SMA, multiple treatment strategies to increase SMN expression can be performed. Targeting SMN production with various pharmacologic compounds, such as antisense oligomers, to either activate the SMN promoter or to alter exon 7-splicing patterns can be performed to improve the phenotype of SMNΔ7 SMA mice. For example, antisense oligonucleotides can block target sequences, including exon splice enhancers or intron splice silencers (ISSs). Furthermore, SMN can be induced postnatally to achieve a therapeutic effect.

Antisense oligomers such as PMO, PMO+, PPMO, and PMO-X, can be delivered to mice via ICV injection at high concentration to alter SMN2 splicing and increase SMN levels. Treated SMA mice may demonstrate improvement in weight gain, motor activity and increased survival time. Antisense oligomers may be delivered by several mechanisms including, but not limited to intracerebroventriclar (ICV) injection, peripheral FV delivery, combined peripheral and ICV delivery and dual ICV injection.

Early CNS treatment will likely yield robust effects. However, delayed CNS delivery may still increase survival levels.

ICV injection may yield an increase in both SMN2 exon 7 incorporation and SMN protein levels in brain and spinal cord. Thus, it may be preferable to restore SMN levels within neurons to have an impact in SMA. It may be possible that long survival benefit can be obtained without significantly enhancing SMN levels in the periphery. However, it is also possible that increasing SMN expression in the autonomic nervous system outside of the blood-brain barrier results in correction of SMA.

TABLE 1

PMO and APN-modified sequences for SMA-targeted oligonucleotides.
APN modified positions are identified in bold and underlined.

| SampleName | Sequence | Sequence Identifier |
|---|---|---|
| N1 | ATT CAC TTT CAT AAT GCT GG | SEQ ID NO: 1 |
| N1-B | ATT CAC TTT CAT AAT GCT GG | SEQ ID NO: 2 |
| N1-C | ATT CAC TTT CAT AAT GCT GG | SEQ ID NO: 3 |
| N1-D | ATT CAC TTT CAT AAT GCT GG | SEQ ID NO: 4 |
| N1-E | ATT CAC TTT CAT AAT GCT GG | SEQ ID NO: 5 |
| N1-F | ATT CAC TTT CAT AAT GCT GG | SEQ ID NO: 6 |
| N1-G | ATT CAC TTT CAT AAT GCT GG | SEQ ID NO: 7 |
| N1-H | ATT CAC TTT CAT AAT GCT GG | SEQ ID NO: 8 |
| AVI-17mer | CAC TTT CAT AAT GCT GG | SEQ ID NO: 9 |
| AVI-17mer-B | CAC TTT CAT AAT GCT GG | SEQ ID NO: 10 |
| AVI-17mer-C | CAC TTT CAT AAT GCT GG | SEQ ID NO: 11 |
| AN/-17mer-D | CAC TTT CAT AAT GCT GG | SEQ ID NO: 12 |
| AVI-17mer-E | CAC TTT CAT AAT GCT GG | SEQ ID NO: 13 |
| AVI-17mer-F | CAC TTT CAT AAT GCT GG | SEQ ID NO: 14 |
| AVI-17mer-G | CAC TTT CAT AAT GCT GG | SEQ ID NO: 15 |
| AVI-17mer-H | CAC TTT CAT AAT GCT GG | SEQ ID NO: 16 |
| AVI-17mer-I | CAC TTT CAT AAT GCT GG | SEQ ID NO: 17 |
| AVI-17mer-J | CAC TTT CAT AAT GCT GG | SEQ ID NO: 18 |
| 14mer | TTT CAT AAT GCT GG | SEQ ID NO: 19 |
| 14mer-B | TTT CAT AAT GCT GG | SEQ ID NO: 20 |
| 14mer-APN | TTT CAT AAT GCT GG | SEQ ID NO: 21 |
| 14mer-C | TTT CAT AAT GCT GG | SEQ ID NO: 22 |
| 14mer-D | TTT CAT AAT GCT GG | SEQ ID NO: 23 |
| 14mer-E | TTT CAT AAT GCT GG | SEQ ID NO: 24 |
| 14mer-F | TTT CAT AAT GCT GG | SEQ ID NO: 25 |
| 3UP11 | AAT GCT GGC AG | SEQ ID NO: 26 |
| 11mer-APN | AAT GCT GGC AG | SEQ ID NO: 27 |
| 11mer-B | AAT GCT GGC AG | SEQ ID NO: 28 |
| 11mer-C | AAT GCT GGC AG | SEQ ID NO: 29 |
| 11mer-D | AAT GCT GGC AG | SEQ ID NO: 30 |
| 11mer-E | AAT GCT GGC AG | SEQ ID NO: 31 |
| 11mer-F | AAT GCT GGC AG | SEQ ID NO: 32 |
| 3UP8 | GCT GGC AG | SEQ ID NO: 33 |
| 8mer-APN | GCT GGC AG | SEQ ID NO: 34 |
| 8mer-B | GCT GGC AG | SEQ ID NO: 35 |
| 8mer-C | GCT GGC AG | SEQ ID NO: 36 |
| 8mer-D | GCT GGC AG | SEQ ID NO: 37 |
| 8mer-E | GCT GGC AG | SEQ ID NO: 38 |
| 8mer-F | GCT GGC AG | SEQ ID N0: 39 |

TABLE 1-continued

PMO and APN-modified sequences for SMA-targeted oligonucleotides.
APN modified positions are identified in bold and underlined.

| SampleName | Sequence | Sequence Identifier |
|---|---|---|
| 8mer-G | G<u>CT</u> <u>GG</u>C <u>A</u>G | SEQ ID NO: 40 |
| 8mer-H | <u>GC</u>T <u>GG</u>C <u>A</u>G | SEQ ID NO: 41 |
| E8/4a | C TAG TAT TTC CTG CAA ATG AG | SEQ ID NO: 42 |
| E8/4a-APN | C <u>T</u>AG <u>T</u>AT TTC C<u>T</u>G CAA A<u>T</u>G AG | SEQ ID NO: 43 |
| E8/4a-B | C <u>T</u>AG <u>T</u>AT <u>T</u>TC C<u>T</u>G CAA A<u>T</u>G AG | SEQ ID NO: 44 |
| E8/4a-C | C <u>T</u>AG TAT <u>T</u>TC C<u>T</u>G C<u>A</u>A A<u>T</u>G AG | SEQ ID NO: 45 |
| E8/4a-D | C <u>T</u>AG TAT <u>T</u>TC C<u>T</u>G C<u>A</u>A A<u>T</u>G <u>A</u>G | SEQ ID NO: 46 |
| E8/4a-E | <u>C</u> <u>T</u>AG <u>T</u>AT <u>T</u>TC C<u>T</u>G C<u>A</u>A A<u>T</u>G AG | SEQ ID NO: 47 |
| E8/4a-F | C <u>T</u>AG <u>T</u>AT TTC CTG C<u>A</u>A A<u>T</u>G AG | SEQ ID NO: 48 |
| E8/4a-G | C <u>T</u>AG <u>T</u>AT TTC CTG CAA A<u>T</u>G AG | SEQ ID NO: 49 |
| E8/4a-H | C TAG TAT <u>T</u>TC C<u>T</u>G CAA A<u>T</u>G AG | SEQ ID NO: 50 |
| E8/4a-I | C TAG TAT <u>T</u>TC C<u>T</u>G C<u>A</u>A ATG AG | SEQ ID NO: 51 |
| E8/4a-J | C TAG TA<u>T</u> <u>T</u>TC C<u>T</u>G C<u>A</u>A ATG AG | SEQ ID NO: 52 |
| E8/4b | C CAG CAT TTC CTG CAA ATG AG | SEQ ID NO: 53 |
| E8/4b-APN | C CAG CA<u>T</u> <u>T</u>TC C<u>T</u>G C<u>A</u>A A<u>T</u>G AG | SEQ ID NO: 54 |
| E8/4b-B | C CAG CA<u>T</u> <u>T</u>TC C<u>T</u>G C<u>A</u>A A<u>T</u>G AG | SEQ ID NO: 55 |
| E8/4b-C | C C<u>A</u>G CAT TTC <u>C</u>TG C<u>A</u>A ATG AG | SEQ ID NO: 56 |
| E8/4b-D | C C<u>A</u>G CAT <u>T</u>TC C<u>T</u>G C<u>A</u>A ATG AG | SEQ ID NO: 57 |
| E8/4b-E | C C<u>A</u>G CA<u>T</u> TTC CTG CAA A<u>T</u>G AG | SEQ ID NO: 58 |
| E8/4b-F | C C<u>A</u>G CA<u>T</u> TTC CTG CAA ATG AG | SEQ ID NO: 59 |
| E8/4b-G | C CAG CAT <u>T</u>TC C<u>T</u>G C<u>A</u>A ATG AG | SEQ ID NO: 60 |
| E8/4b-H | C CAG CAT <u>TT</u>C C<u>T</u>G C<u>A</u>A <u>A</u>TG AG | SEQ ID NO: 61 |
| E8/3 | A TGC CAG CAT TTC CTG CAA ATG AGA | SEQ ID NO: 62 |
| E8/3-B | A <u>T</u>GC CAG CA<u>T</u> TTC C<u>T</u>G CAA A<u>T</u>G AGA | SEQ ID NO: 63 |
| E8/3-C | A <u>T</u>GC CAG CAT TTC C<u>T</u>G C<u>A</u>A A<u>T</u>G AGA | SEQ ID NO: 64 |
| E8/3-D | A <u>T</u>GC C<u>A</u>G CA<u>T</u> TTC C<u>T</u>G C<u>A</u>A A<u>T</u>G AGA | SEQ ID NO: 65 |
| E8/3-E | A <u>T</u>GC C<u>A</u>G <u>C</u>AT TTC C<u>T</u>G C<u>A</u>A A<u>T</u>G AGA | SEQ ID NO: 66 |
| E8/3-F | A <u>T</u>GC C<u>A</u>G CAT <u>T</u>TC C<u>T</u>G C<u>A</u>A A<u>GA</u> | SEQ ID NO: 67 |
| E8/3-G | A <u>T</u>GC CAG CAT TTC C<u>T</u>G CAA A<u>T</u>G AGA | SEQ ID NO: 68 |
| E8/3-H | A <u>T</u>GC CAG CAT TTC CTG CAA A<u>T</u>G AGA | SEQ ID NO: 69 |
| E8/4 | GCT CTA TGC CAG CAT TTC CTG CAA A | SEQ ID NO: 70 |
| E8/4-B | GCT C<u>T</u>A TGC CAG CAT TTC C<u>T</u>G CAA A | SEQ ID NO: 71 |
| E8/4-C | GCT C<u>T</u>A TGC CAG CA<u>T</u> TTC C<u>T</u>G CAA A | SEQ ID NO: 72 |
| E8/4-D | GCT C<u>T</u>A TGC C<u>A</u>G CA<u>T</u> TTC C<u>T</u>G CAA A | SEQ ID NO: 73 |
| E8/4-E | GC<u>T</u> C<u>T</u>A TGC CAG CAT TTC C<u>T</u>G C<u>A</u>A A | SEQ ID NO: 74 |
| E8/4-F | GCT CTA TG<u>C</u> C<u>A</u>G C<u>AT</u> <u>T</u>TC CTG CAA A | SEQ ID NO: 75 |
| E8/4-G | GC<u>T</u> <u>C</u>TA TGC CAG CA<u>T</u> TTC C<u>T</u>G CAA A | SEQ ID NO: 76 |
| E8/4-H | GC<u>T</u> <u>C</u>TA TGC CAG CA<u>T</u> <u>T</u>TC CTG CAA A | SEQ ID NO: 77 |
| E8/4-I | GC<u>T</u> <u>C</u>TA TGC CAG CA<u>T</u> <u>T</u>TC C<u>T</u>G CAA A | SEQ ID NO: 78 |
| E8/4-J | GC<u>T</u> C<u>T</u>A TGC CAG CA<u>T</u> <u>T</u>TC CTG C<u>A</u>A A | SEQ ID NO: 79 |

What is claimed:

1. An antisense oligonucleotide of 10-40 nucleotides in length which specifically hybridizes to a region within the SMN2 gene, such that the level of exon 7-containing SMN2 mRNA relative to exon 7-deleted SMN2 mRNA in the cell is enhanced, wherein the antisense oligonucleotide is a morpholino oligonucleotide, and wherein each nucleotide is a nucleotide having a formula:

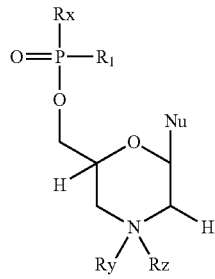

wherein Nu is a nucleobase;
$R_1$ is a moiety of the formula (I):

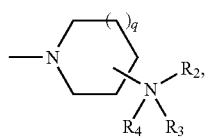

(I)

or
$R_1$ is —$N(CH_3)_2$;
q is 0, 1, 2, 3 or 4;
$R_2$ is selected from the group consisting of hydrogen, $C_1$-$C_5$ alkyl, and a formamidinyl moiety, and
$R_3$ is selected from the group consisting of hydrogen and $C_1$-$C_5$ alkyl, or
$R_2$ and $R_3$ are joined to form a 5-7 membered heterocyclic ring optionally containing an oxygen hetero atom, where the ring may be optionally substituted with a substituent selected from the group consisting of $C_1$-$C_5$ alkyl, phenyl, halogen, and aralkyl;
$R_4$ is selected from the group consisting of null, hydrogen, a $C_1$-$C_6$ alkyl and aralkyl;
$R_x$ is selected from the group consisting of HO—, a nucleotide, and piperazinyl;
$R_y$ is selected from the group consisting of hydrogen, a $C_1$-$C_6$ alkyl, a nucleotide, a, an amino acid, a formamidinyl moiety, and acyl; and,
$R_z$ is selected from the group consisting of null, hydrogen, a $C_1$-$C_6$ alkyl, and acyl; and pharmaceutically acceptable salts thereof,
wherein at least one $R_1$ is of formula (I).

2. The antisense oligonucleotide of claim 1, wherein at least one nucleotide has the formula:

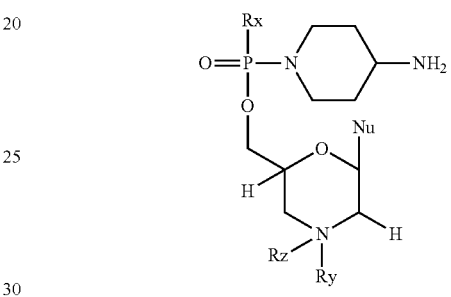

wherein Rx, Ry, Rz, and Nu are as stated in claim 1.

3. The antisense oligonucleotide of claim 1, wherein the target region is within exon 7, intron 7, or exon 8 of the SMN2 gene.

4. The antisense oligonucleotide of claim 3, wherein the antisense oligonucleotide comprises a sequence which is complementary to a target region within intron 7 of the SMN2 gene.

5. The antisense oligonucleotide of claim 1, wherein the antisense oligonucleotide comprises a sequence which is complementary to a portion of intron 7 and exon 8 of the SMN2 gene.

6. The antisense oligonucleotide of claim 1, wherein the antisense oligonucleotide comprises a sequence of from about 10 to about 30 nucleotides.

7. The antisense oligonucleotide of claim 1, wherein the antisense oligonucleotide comprises a sequence of from about 14 to about 21 nucleotides.

8. The antisense oligonucleotide of claim 1, wherein the antisense oligonucleotide comprises a sequence selected from SEQ ID NOS: 2-8, 10-18, 20-25, 27-32, 34-41, 43-52, 54-61, 63-69, and 71-79.

9. A method of enhancing the level of exon 7-containing SMN2 mRNA relative to exon-deleted SMN2 mRNA in a cell, comprising contacting the cell with an antisense oligonucleotide of 10-40 nucleotides in length which specifically hybridizes to a region within the SMN2 gene, such that the level of exon 7-containing SMN2 mRNA relative to exon 7-deleted SMN2 mRNA in the cell is enhanced, wherein the antisense oligonucleotide is a morpholino oligonucleotide, and wherein each nucleotide is a nucleotide having a formula:

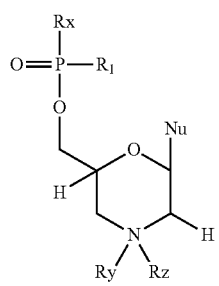

wherein Nu is a nucleobase;
$R_1$ is a moiety of the formula (I):

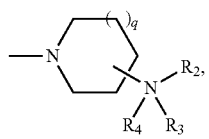

or
$R_1$ is —$N(CH_3)_2$;
q is 0, 1, 2, 3 or 4;
$R_2$ is selected from the group consisting of hydrogen, $C_1$-$C_5$ alkyl, and a formamidinyl moiety, and
$R_3$ is selected from the group consisting of hydrogen and $C_1$-$C_5$ alkyl, or
$R_2$ and $R_3$ are joined to form a 5-7 membered heterocyclic ring optionally containing an oxygen hetero atom, where the ring may be optionally substituted with a substituent selected from the group consisting of $C_1$-$C_5$ alkyl, phenyl, halogen, and aralkyl;
$R_4$ is selected from the group consisting of null, hydrogen, a $C_1$-$C_6$ alkyl and aralkyl;
$R_x$ is selected from the group consisting of HO—, a nucleotide, and piperazinyl;
$R_y$ is selected from the group consisting of hydrogen, a $C_1$-$C_6$ alkyl, a nucleotide, a an amino acid, a formamidinyl moiety, and acyl; and,
$R_z$ is selected from the group consisting of null, hydrogen, a $C_1$-$C_6$ alkyl, and acyl; and pharmaceutically acceptable salts thereof,
wherein at least one $R_1$ is of formula (I).

10. The method of claim 9, wherein at least one nucleotide has the formula:

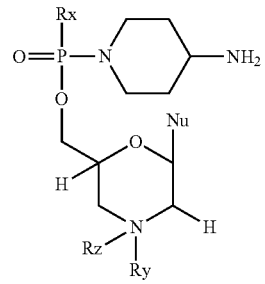

wherein Rx, Ry, Rz, and Nu are as stated in claim 9.

11. The method of claim 10, wherein Nu is thymine or uracil.

12. The method of claim 9, wherein the target region is within exon 7, intron 7, or exon 8 of the SMN2 gene.

13. The method of claim 12, wherein the antisense oligonucleotide comprises a sequence which is complementary to intron 7 of the SMN2 gene.

14. The method of claim 13, wherein the antisense oligonucleotide comprises a sequence which is complementary to a portion of intron 7 and exon 8 of the SMN2 gene.

15. The method of claim 9, wherein the antisense oligonucleotide comprises a sequence of from about 10 to about 30 nucleotides.

16. The method of claim 9, wherein the antisense oligonucleotide comprises a sequence of from about 14 to about 21 nucleotides.

17. The method of claim 9, wherein the antisense oligonucleotide comprises a sequence selected from SEQ ID NOS: 2-8, 10-18, 20-25, 27-32, 34-41, 43-52, 54-61, 63-69, and 71-79.

18. A method of treating spinal muscular atrophy (SMA) in a patient, comprising administering to the patient an antisense oligonucleotide according to claim 1, thereby treating the patient.

* * * * *

UNITED STATES PATENT AND TRADEMARK OFFICE
CERTIFICATE OF CORRECTION

PATENT NO. : 9,944,926 B2
APPLICATION NO. : 14/360895
DATED : April 17, 2018
INVENTOR(S) : Peter Linsley et al.

Page 1 of 1

It is certified that error appears in the above-identified patent and that said Letters Patent is hereby corrected as shown below:

In the Claims

In Claim 1, Column 69, Line 66, "a, an amino acid" should read "an amino acid"

In Claim 9, Column 71, Line 36, "a, an amino acid" should read "an amino acid"

Signed and Sealed this
Twenty-sixth Day of June, 2018

Andrei Iancu
*Director of the United States Patent and Trademark Office*